(12) United States Patent
Brown

(10) Patent No.: US 6,270,455 B1
(45) Date of Patent: Aug. 7, 2001

(54) NETWORKED SYSTEM FOR INTERACTIVE COMMUNICATIONS AND REMOTE MONITORING OF DRUG DELIVERY

(75) Inventor: Stephen J. Brown, Woodside, CA (US)

(73) Assignee: Health Hero Network, Inc., Mountain View, CA (US)

(*) Notice: Subject to any disclaimer, the term of this patent is extended or adjusted under 35 U.S.C. 154(b) by 0 days.

(21) Appl. No.: 09/201,441

(22) Filed: Nov. 30, 1998

Related U.S. Application Data

(63) Continuation-in-part of application No. 08/946,341, filed on Oct. 7, 1997, now Pat. No. 5,997,476, which is a continuation-in-part of application No. 08/847,009, filed on Apr. 30, 1997, now Pat. No. 5,897,493.
(60) Provisional application No. 60/041,746, filed on Mar. 28, 1997, and provisional application No. 60/041,751, filed on Mar. 28, 1997.

(51) Int. Cl.[7] .......................................... A61B 5/00
(52) U.S. Cl. ........................... 600/300; 600/365; 128/920
(58) Field of Search .................................. 600/300, 301, 600/481–486, 500, 529, 348, 361, 365, 538, 544; 128/897–898, 904, 905, 920–925

(56) References Cited

U.S. PATENT DOCUMENTS

| | | | |
|---|---|---|---|
| 4,253,521 | 3/1981 | Savage | 166/123 |
| 4,950,246 | 8/1990 | Muller | 604/154 |
| 5,019,974 | 5/1991 | Beckers | 364/413.02 |
| 5,128,752 | 7/1992 | Von Kohorn | 358/84 |
| 5,176,502 | 1/1993 | Sanderson et al. | 417/18 |
| 5,329,459 | 7/1994 | Kaufman et al. | 364/479 |
| 5,434,611 | 7/1995 | Tamura | 348/8 |

(List continued on next page.)

FOREIGN PATENT DOCUMENTS

| | | | |
|---|---|---|---|
| 0251520 | 6/1987 | (EP) | 15/42 |
| 0370599 | 7/1989 | (EP) | . |
| 9509386 | 4/1995 | (WO) | . |
| 9520199 | 7/1995 | (WO) | . |
| 9708605 | 3/1997 | (WO) | . |
| 9712544 | 4/1997 | (WO) | . |

OTHER PUBLICATIONS

Giuffrida, A., Should we pay the patient? Review of financial incentives to enhance patient compliance, Biomedical Journal, vol. 315, pp. 703–707, 1997.

*Primary Examiner*—Max Hindenburg
*Assistant Examiner*—Michael Astorino
(74) *Attorney, Agent, or Firm*—Black Lowe & Graham PLLC

(57) ABSTRACT

A networked system for communicating information to a patient and for remotely monitoring the patient. The system includes a server and a remote interface for entering in the server a set of queries to be answered by the patient. The server may be a web server and the remote interface may be a personal computer or remote terminal connected to the server via the Internet. The system also includes a measurement apparatus for providing measurement data related to a patient's condition and treatment, and a remotely programmable apparatus connected to the server via a communication network, such as the Internet. The remotely programmable apparatus interacts with the patient in accordance with a script program received from the server. The server includes a script generator for generating the script program from the set of queries entered through the remote interface. The script program is received and executed by the remotely programmable apparatus to communicate the queries to the patient, to receive responses to the queries, and to transmit the responses from the apparatus to the server. The measurement data provided by the measurement apparatus may include physiological condition data and drug delivery measurement data for paperless recordation at a remote location.

44 Claims, 31 Drawing Sheets

U.S. PATENT DOCUMENTS

| | | | |
|---|---|---|---|
| 5,441,047 | 8/1995 | David et al. | 128/670 |
| 5,569,212 | 10/1996 | Brown | 604/207 |
| 5,628,309 | 5/1997 | Brown | 128/632 |
| 5,704,902 | 1/1998 | Vanderbelt et al. | 601/72 |
| 5,720,733 | 2/1998 | Brown | 604/207 |
| 5,782,814 | 7/1998 | Brown et al. | 604/207 |
| 5,792,117 | 8/1998 | Brown | 604/207 |
| 5,868,669 * | 2/1999 | Lliff | 600/300 |

* cited by examiner

SCRIPT ENTRY SCREEN

SCRIPT NAME: DIABETES SCRIPT 1

| QUERIES | CHOICE 1 | CHOICE 2 | CHOICE 3 | CHOICE 4 |
|---|---|---|---|---|
| HOW DO YOU FEEL? | VERY BAD | BAD | GOOD | VERY GOOD |
| HOW WELL ARE YOU MANAGING YOUR DISEASE? | VERY BADLY | BADLY | WELL | VERY WELL |
| HOW HARD IS IT FOR YOU TO FOLLOW YOUR TREATMENT PLAN? | VERY HARD | HARD | EASY | VERY EASY |
| HOW HARD IS IT FOR YOU TO CONTROL YOUR BLOOD SUGAR? | VERY HARD | HARD | EASY | VERY EASY |

SELECT DEVICE TYPE(S)

[X] GLUCOSE METER  [ ] RESPIRATORY FLOW METER  [ ] BP CUFF

CONNECTION TIME: 03:00 ▽   CREATE SCRIPT   CANCEL

*Fig. 5*

NUMBER: 9001 {LF}

LED: 1 {LF}

ZAP: {LF}

CLS: {LF}

DISPLAY: ANSWER QUERIES NOW?
        PRESS ANY BUTTON TO START {LF}

WAIT: {LF}

CLS: {LF}

DISPLAY: HOW DO YOU FEEL?

VERY            VERY
        BAD   BAD   GOOD   GOOD {LF}

INPUT: OOOO {LF}

CLS: {LF}

DISPLAY: HOW WELL ARE YOU
        MANAGING YOUR DISEASE?
        VERY            VERY
        WELL   BADLY   WELL   WELL {LF}

INPUT: OOOO {LF}

CLS: {LF}

DISPLAY: HOW HARD IS IT FOR YOU TO
        FOLLOW YOUR TREATMENT PLAN?
        VERY            VERY
        HARD   HARD   EASY   EASY {LF}

INPUT: OOOO {LF}

CLS: {LF}

DISPLAY: HOW HARD IS IT FOR YOU TO
        CONTROL YOUR BLOOD SUGAR?
        VERY            VERY
        HARD   HARD   EASY   EASY {LF}

*Fig. 6A*

INPUT: OOOO {LF}

CLS: {LF}

DISPLAY: CONNECT GLUCOSE METER
    AND PRESS ANY BUTTON
    WHEN FINISHED {LF}

WAIT: {LF}

CLS: {LF}

DISPLAY: COLLECTING MEASUREMENTS {LF}

COLLECT: GLUCOSE_METER {LF}

CLS: {LF}

DISPLAY: CONNECT APPARATUS TO
    TELEPHONE JACK AND
    PRESS ANY BUTTON
    WHEN FINISHED {LF}

WAIT: {LF}

LED: 0 {LF}

CLS: {LF}

DELAY: 03:00 {LF}

DISPLAY: CONNECTING TO SERVER {LF}

CONNECT: {LF}

{EOF}

*Fig. 6B*

PATIENT REPORT

PATIENT: LINDSEY, DAN  DATE OF MEASUREMENT: MARCH 15, 1997

QUERY RESPONSES

HOW DO YOU FEEL? BAD

HOW WELL ARE YOU MANAGING YOUR DISEASE? BADLY

HOW HARD IS IT FOR YOU TO FOLLOW YOUR TREATMENT PLAN? HARD

HOW HARD IS IT FOR YOU TO CONTROL YOUR BLOOD SUGAR? VERY HARD

*Fig. 10*

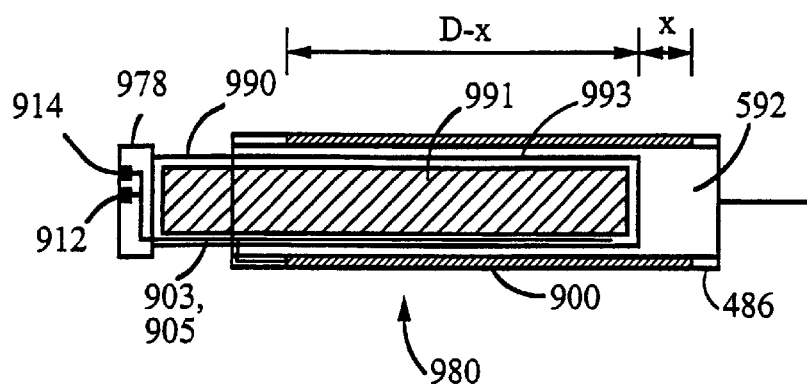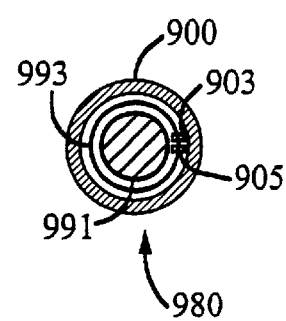
*Fig. 27A*   *Fig. 27B*

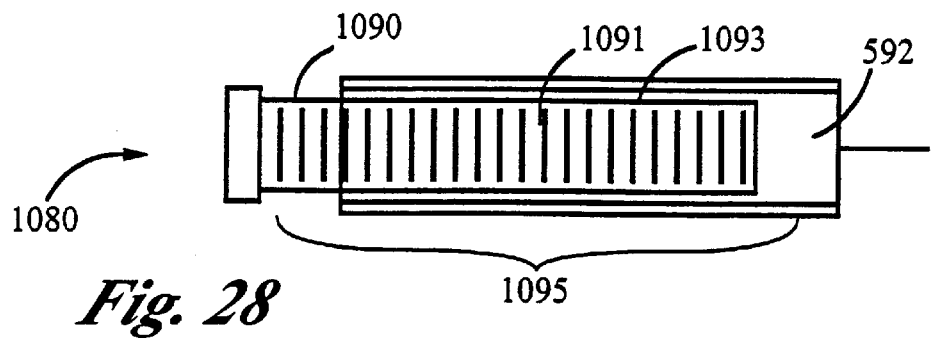
*Fig. 28*
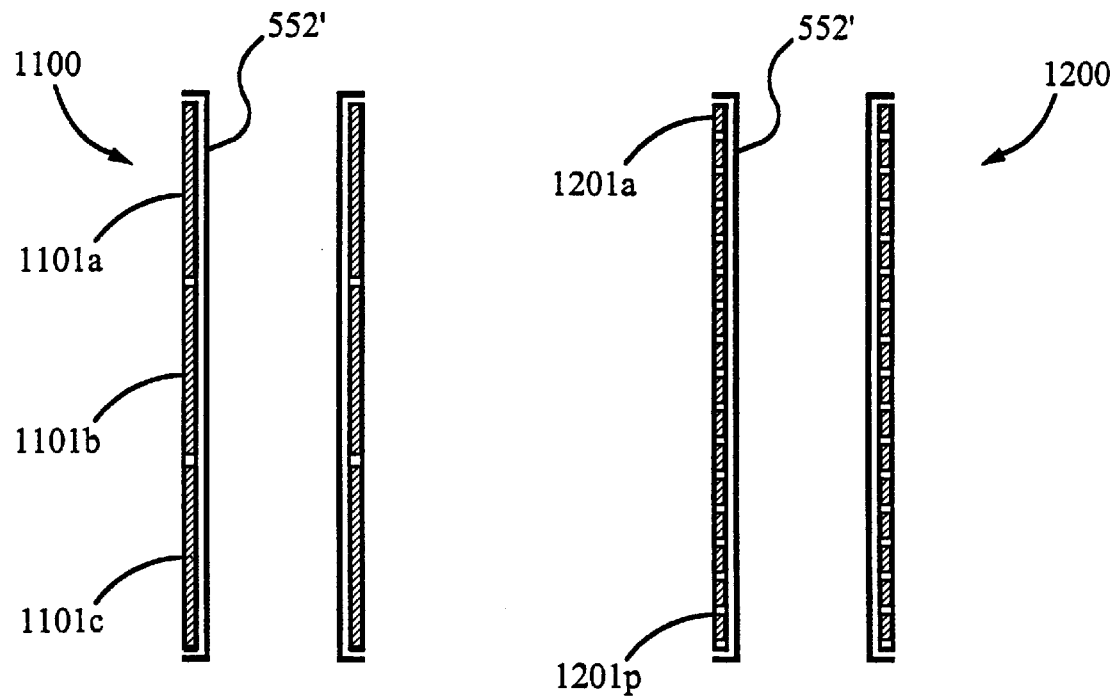
*Fig. 29A*   *Fig. 29B*

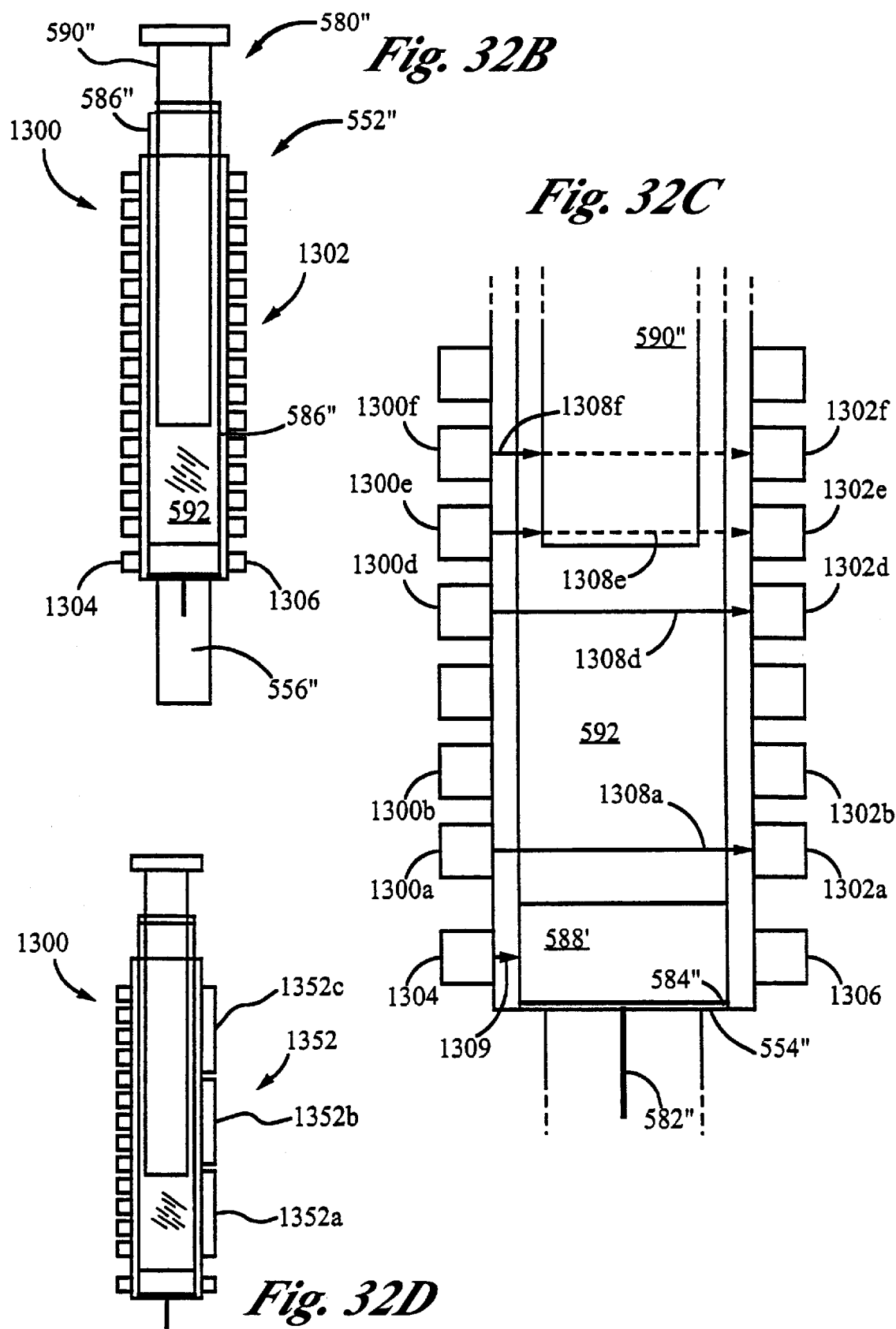

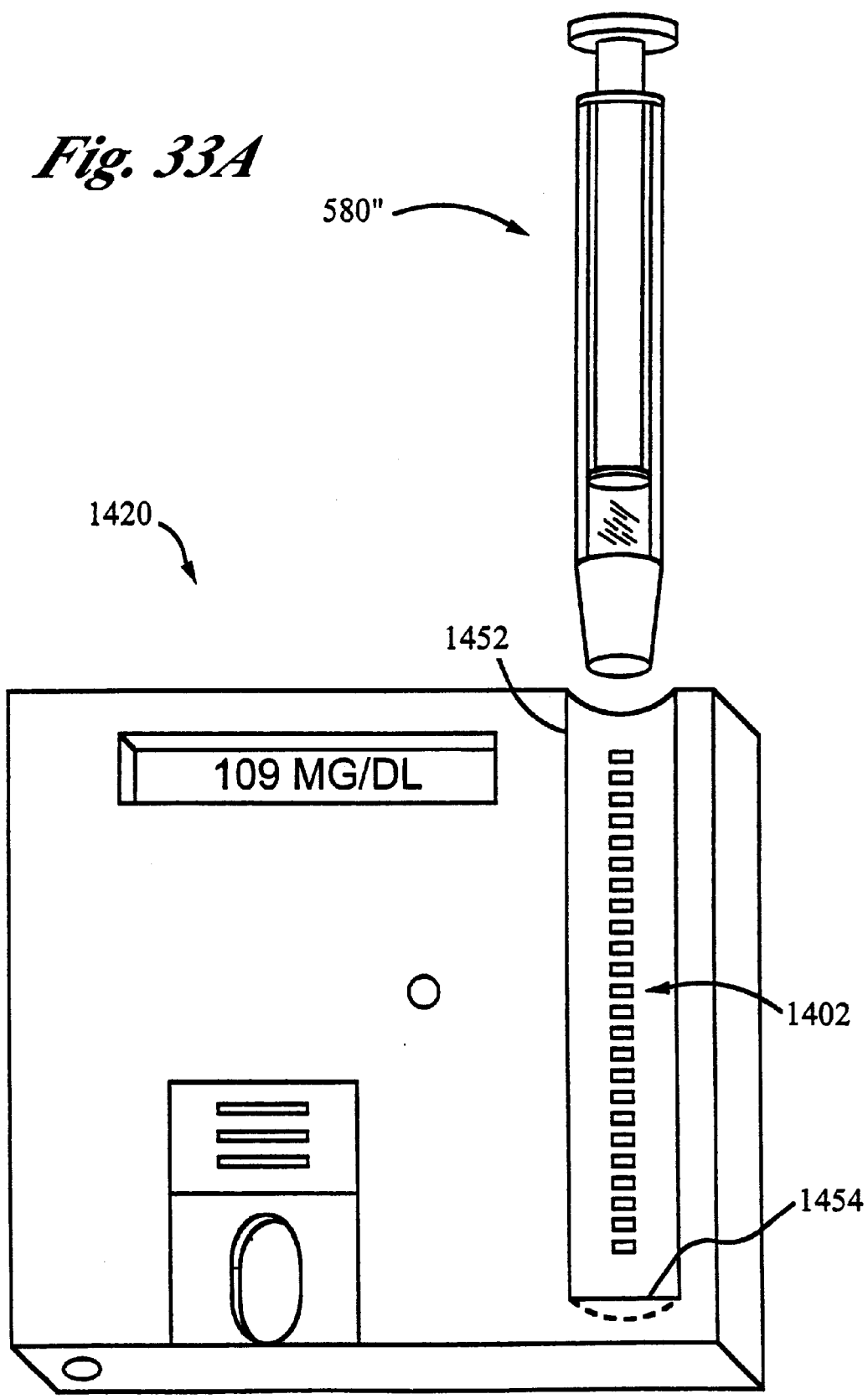

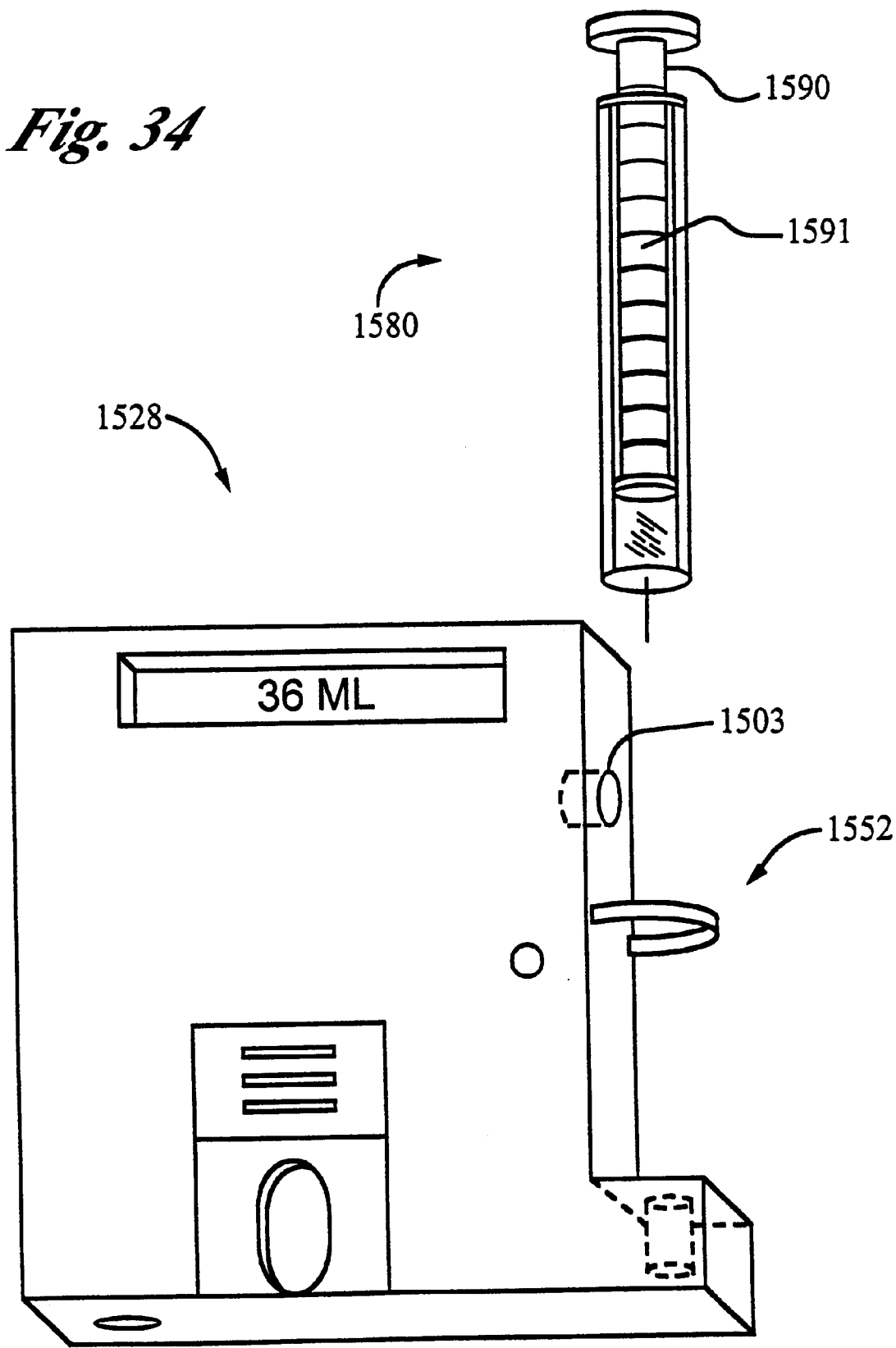

NETWORKED SYSTEM FOR INTERACTIVE COMMUNICATIONS AND REMOTE MONITORING OF DRUG DELIVERY

RELATED U.S. APPLICATION DATA

This application is a continuation-in-part of application Ser. No. 08/946,341, filed Oct. 7, 1997 which is now U.S. Pat. No. 5,997,476 is a continuation-in-part application of application Ser. No. 08/847,009 filed Apr. 30, 1997 is now U.S. Pat. No. 5,897,493. The parent application claims priority from provisional application Ser. No. 60/041,746 filed Mar. 28, 1997 and from provisional application Ser. No. 60/041,751 filed Mar. 28, 1997. All of the above named applications are incorporated by reference herein.

FIELD OF THE INVENTION

The present invention relates generally to communication systems for remote monitoring of patients, and in particular to a networked system for remotely monitoring patients and for communicating information to the patients through the use of script programs. The invention further relates to a patient monitoring and drug delivery measurement system for measuring and electronically recording measurements of drug dose(s) administered to a patient. The invention also relates to injection syringes adapted for use with a dose measurement apparatus for electronically recording drug delivery measurements.

BACKGROUND OF THE INVENTION
Remote Communication and Monitoring Systems

In the United States alone, over 100 million people have chronic health conditions, accounting for an estimated $700 billion in annual medical costs. In an effort to control these medical costs, many healthcare providers have initiated outpatient or home healthcare programs for their patients. The potential benefits of these programs are particularly great for chronically ill patients who must treat their diseases on a daily basis. However, the success of these programs is dependent upon the ability of the healthcare providers to monitor the patients remotely to avert medical problems before they become complicated and costly. Unfortunately, no convenient and cost effective monitoring system exists for those patients who have the greatest need for monitoring—the poor and the elderly.

Prior attempts to monitor patients remotely have included the use of personal computers and modems to establish communication between patients and healthcare providers. However, computers are too expensive to give away and the patients who already own computers are only a small fraction of the total population. Further, the patients who own computers are typically young, well educated, and have good healthcare coverage. Thus, these patients do not have the greatest unmet medical needs. The patients who have the greatest unmet medical needs are the poor and elderly who do not own computers or who are unfamiliar with their use.

Similar attempts to establish communication between patients and healthcare providers have included the use of the Internet and internet terminals. Although internet terminals are somewhat less costly than personal computers, they are still too expensive to give away to patients.

Moreover, monthly on-line access charges are prohibitive for poor patients.

Other attempts to monitor patients remotely have included the use of medical monitoring devices with built-in modems. Examples of such monitoring devices include blood glucose meters, respiratory flow meters, and heart rate monitors. Unfortunately, these monitoring devices are only designed to collect physiological data from the patients. They do not allow flexible and dynamic querying of the patients for other information, such as quality of life measures or psycho-social variables of illness. Nor do they allow for remote monitoring or recording of drug dose(s) administered to, or self-administered by, a patient.

Prior attempts to monitor patients remotely have also included the use of interactive telephone or video response systems. Such interactive systems are disclosed in U.S. Pat. No. 5,390,238 issued to Kirk et al. on Feb. 14, 1995, U.S. Pat. No. 5,434,611 issued to Tamura on Jul. 18, 1995, and U.S. Pat. No. 5,441,047 issued to David et al. on Aug. 15, 1995. One disadvantage of these systems is that they either require a patient to call in to a central facility to be monitored or require the central facility to call the patient according to a rigid monitoring schedule.

If the patients are required to call the central facility, only the compliant patients will actually call regularly to be monitored. Non-compliant patients will typically wait until an emergency situation develops before contacting their healthcare provider, thus defeating the purpose of the monitoring system. If the central facility calls each patient according to a monitoring schedule, it is intrusive to the patient's life, and resistance to the monitoring program grows over time.

Another disadvantage of these conventional interactive response systems is that they are prohibitively expensive for poor patients. Further, it is difficult to identify each patient uniquely using these systems. Moreover, these systems are generally incapable of collecting medical data from monitoring devices, such as blood glucose meters, respiratory flow meters, or heart rate monitors.

Remote Monitoring of Drug Delivery

In recent years, the value of keeping electronic medical records in place of paper records has been widely recognized in the health care industry. The use of electronic medical records allows health care providers and patients to store, retrieve, and share medical information with considerably more ease and accuracy. The sharing of medical information is particularly important in treatment programs involving the injection of insulin, human growth hormone, or other medications.

Typically, these injections are performed using disposable syringes. Unfortunately, no adequate apparatus exists that measures and electronically records dose information from a disposable syringe. As a result, the patient or health care worker performing the injection is burdened with the task of injecting the dose and then manually recording the dose amount in a logbook.

Because of the frequency of such injections, often several times a day for diabetics, it becomes difficult for a patient to keep accurate records. Indeed, studies have shown that a patient's own records and recollections are often incomplete and inaccurate. Additionally, a patient may intentionally cheat while making self-recorded entries in an attempt to create a logbook that will please his or her doctor. In the long-term this makes patient monitoring extremely difficult and jeopardizes the treatment program, possibly even endangering the patient's life.

Attempts have been made to develop electronic management systems for assisting patients in self-administered drug programs. For example, U.S. Pat. No. 5,019,974 issued to Beckers describes a hand-held, microprocessor-based recorder that interfaces with a master computer. The patient enters therapy information into the recorder via a keyboard. The recorder includes a display for displaying treatment therapy guidelines to the patient. The recorder also has a blood glucose meter for recording the patient's blood glucose levels.

The recorder described by Beckers does not automatically measure and record dose information from a disposable syringe. After injecting a dose, the patient must manually enter the dose information into the recorder using switches or keys. Although this is an improvement over keeping written records on paper, the effectiveness of the drug program is still limited by the patient's recollections and recordings, which are unreliable.

Attempts have also been made to develop devices that deliver a predetermined dose of medication and record the dose amount. For example, U.S. Pat. No. 5,176,502 issued to Sanderson et al. on Jan. 5, 1993 describes a syringe pump for expelling a preset dose of medication from a syringe. The syringe pump includes a syringe retainer for holding the syringe and a driver for engaging the plunger of the syringe. An electric motor pushes the driver and plunger into the syringe barrel to expel the medication.

The syringe pump further includes a monitoring circuit for monitoring the motion of the driver during the delivery of the medication. The monitoring circuit includes a linear potentiometer having an electrically conductive strip of resistive material. The resistive material is positioned such that it engages an electrical contact of the driver. The position of the electrical contact on the resistive strip varies the voltage of the monitoring circuit, thus indicating the position of the plunger inside the barrel. A microprocessor receives voltage signals from the monitoring circuit and compares the voltage signals to preprogrammed signals to determine if the plunger displacement corresponds to correct displacement for delivering the preset dose. A control mechanism connected to the microprocessor regulates the driver's movement to ensure the preset dose of medication is delivered.

Although the syringe pump described by Sanderson does allow electronic recording of dose information, it is only designed to deliver medication directly into an intravenous line. It is not designed to inject a patient directly nor can it measure and record a dose from a syringe unless the syringe pump pushes the plunger. Consequently, the syringe pump is of little use to a health care worker who must inject a patient directly, or to an outpatient who must follow a self-injection treatment program.

Another device for injecting a preset dose of medication and for recording the injected dose is disclosed in U.S. Pat. No. 4,950,246 issued to Muller on Aug. 21, 1990. Muller describes a battery-operated injection pen having a pump rod driven by an electric motor. The electric motor is controlled by an electronic control unit that includes a microprocessor with a memory for storing dose information. The injection pen further includes a sensor connected to the control unit for electrically determining the position of the pump rod, and thus the amount of medication injected.

Although the injection pen described by Muller measures and electronically records dose information, it has several injection pen is an expensive device requiring complicated electronic equipment to deliver and record doses. Moreover, because the injection pen integrates a syringe and electronic recorder into one device, it is not disposable. The patient must use it repeatedly for each injection, even after the injection pen has been contaminated with blood. Consequently, the injection pen does not provide an inexpensive, convenient, or hygienic solution to patients wishing to measure and electronically record injected dose information.

U.S. Pat. No. 4,853,521 to Claeys presents a programmable, intelligent reader unit which receives and records drug data using hand-held or fixed scanners. The scanners read bar codes in place on syringes, ampoules, flow meters, etc. In addition, this intelligent reader allows the user to weigh a syringe before and after injection to determine and record the administered amount of medicine. Dosage data logged in this manner can be displayed or printed out in the form of a record.

Operating the device described by Claeys requires many complicated steps of weighing syringes, scanning in bar codes, etc. The complexity of the required procedures, as well as the high cost of the apparatus, have precluded its widespread use. Additionally, the device cannot be easily carried by the user for recording doses while away from the health care facility or home. Thus, no inexpensive apparatus exists for determining and electronically recording dose information from a disposable syringe. Further, no such apparatus exists that is both simple in operation and easily carried by a user.

The following U.S. patents are incorporated by reference herein: U.S. Pat. No. 5,569,212; U.S. Pat. No. 5,628,309; U.S. Pat. No. 5,704,902; U.S. Pat. No. 5,720,733; U.S. Pat. No. 5,782,814; and U.S. Pat. No. 5,792,117. The following patent applications are also incorporated by reference herein: Ser. No. 08/972,670; Ser. No. 08/972,375; Ser. No. 08/898,711; and Ser. No. US97/12966.

OBJECTS AND ADVANTAGES OF THE INVENTION

In view of the above, it is an object of the present invention to provide a simple and inexpensive system for remotely monitoring patients and for communicating information to the patients. It is another object of the invention to provide a system which allows flexible and dynamic querying of the patients. It is a further object of the invention to provide a system which combines querying of patients with medical device monitoring in the same monitoring session. Another object of the invention is to provide a monitoring system which incurs lower communications charges than those incurred by conventional monitoring systems. A further object of the invention is to provide a monitoring system which may be used at any time convenient for a patient.

It is a further object of the present invention to provide a system which combines interactive communication between a healthcare provider and a patient at a remote location, with measurement and paperless recordation of drug dose(s) administered to the patient. It is a further object of the invention to provide an apparatus for inductively, capacitively, or optically determining, and for electronically recording, an injection dose delivered to a patient from a disposable syringe. It is another object of the invention to provide a drug dose measurement and patient monitoring apparatus that may be easily operated and carried by a user. A further object of the invention is to provide a patient monitoring and drug delivery measurement apparatus suited to diabetic patients, and to diabetes home care in particular. It is yet another object to provide an apparatus facilitating automated paperless data processing, from measurements performed by the patient to the recording at the clinic.

These and other objects and advantages will become more apparent after consideration of the ensuing description and the accompanying drawings.

SUMMARY OF THE INVENTION

The invention presents a networked system for remotely monitoring an individual, for communicating information to the individual, and for recording patient related data generated at a remote location. The system includes a server and a remote interface for entering in the server a set of queries to be answered by the individual. The server is preferably a worldwide web server and the remote interface is preferably a personal computer or network terminal connected to the web server via the Internet. The system also includes a remotely programmable apparatus for interacting with the individual. The remotely programmable apparatus is connected to the server via a communication network, preferably the Internet. The apparatus interacts with the individual in accordance with a script program received from the server. The server may also receive patient-related data from the remotely programmable apparatus via the communication network.

The server includes a script generator for generating the script program from the queries entered through the remote interface. The script program is executable by the remotely programmable apparatus to communicate the queries to the individual, to receive responses to the queries, and to transmit the responses from the remotely programmable apparatus to the server. The server also includes a database connected to the script generator for storing the script program and the responses to the queries.

The remotely programmable apparatus has a communication device, such as a modem, for receiving the script program from the server and for transmitting the responses and/or patient related data to the server. The remotely programmable apparatus also has a user interface for communicating the queries to the individual and for receiving the responses to the queries from the individual. In a preferred embodiment, the user interface includes a display for displaying the queries and user input buttons for entering the responses to the queries. In an alternative embodiment, the user interface includes a speech synthesizer for audibly communicating the queries and a speech recognizer for receiving spoken responses to the queries.

The remotely programmable apparatus also includes a memory for storing the script program and the responses to the queries. The remotely programmable apparatus further includes a microprocessor connected to the communication device, the user interface, and the memory. The microprocessor executes the script program to communicate the queries to the individual, to receive the responses to the queries, and to transmit the responses to the server through the communication network.

In one embodiment, the system also includes at least one monitoring device for producing measurements of a physiological condition of the individual and for transmitting the measurements to the apparatus.

According to another embodiment, a communication and monitoring system includes a patient monitoring and drug delivery measurement apparatus, in communication with the remotely programmable apparatus for providing measurements of drug dose(s) administered to, or self-administered by, a patient, wherein the communication and monitoring system includes: a server, a communications network, and a remotely programmable apparatus; and wherein the patient monitoring and drug delivery measurement apparatus includes; a dose measurement unit or element, a measuring device, a calibration memory, and a recording device.

A patient monitoring system of the invention may further include a device interface connected to the microprocessor for receiving physiological condition and/or drug delivery measurements from the drug delivery measurement apparatus. The measurements are stored in the memory and transmitted to the server with the responses to the queries. The server also preferably includes a report generator connected to the database for generating a report of the measurements and responses. The report is displayed on the remote interface.

According to one embodiment, the invention provides a system for non-invasively measuring and electronically recording a dose of a drug or medication delivered to a patient from a syringe. A currently preferred patient monitoring and drug delivery measurement system comprises apparatus for measuring and electronically recording a dose of a drug administered to a patient from a syringe, wherein the dose delivered from the syringe m ay be measured inductively, capacitively, or optically. There now follows a summary description of three different embodiments of a drug dose measurement apparatus, each for use in conjunction with a patient monitoring system of the invention.

i) Optical Dose Measurement

In one embodiment of the invention, there is provided an apparatus for optically measuring a dose of a drug delivered to a patient, the apparatus including: a holding means for receiving and holding the syringe, a light source in optical communication with the syringe, an optical detector in optical communication with the syringe, and a recording means in electrical communication with the optical detector. An alignment means aligns the syringe barrel to the optical detector and/or the light source, when the syringe is in a measurement position.

The light source generates light incident on the syringe. An optical response of the syringe to the incident light is indicative of the liquid quantity within the syringe, and implicitly of the dose administered (or to be administered) from the syringe. The optical detector detects the optical response. The recording means records a dose datum indicative of the optical response and the dose. The dose can be computed from the optical response in conjunction with calibration or syringe parameter data, as will be described in detail hereinbelow.

The incident light preferably includes wavelengths that are suitable for measuring typical plunger displacements (resolution on the order of 0.1 mm to 1 mm) and/or liquid quantities within the syringe (resolution on the order of 0.1 $cm^3$), and that interact minimally with elements of the syringe (e.g. the barrel) which do not vary with the quantity of liquid within the syringe. Such wavelengths are preferably, but generally need not be, in the visible or near-visible (infrared/ultraviolet) ranges. Preferably, the detector is suitable for detecting light within a range of wavelengths emitted by the light source. Generally, the wavelength range emitted by the light source need not be identical to the wavelength range detected by the detector. In fact, the wavelength ranges need not even overlap, if the light detected by the detector results from absorption and re-emission by the syringe.

The light source and detector preferably comprise semiconductor emitting/detecting devices, but generally may include any device capable of emitting/detecting light of desired wavelengths. Such devices may include antennas or heat sensors. The recording means includes an electronic memory, preferably a digital memory unit.

The detector preferably includes a plurality of longitudinally spaced individual optical detecting elements coupled to the holding means and in optical communication with the syringe. The detecting elements detect an optical response pattern of the syringe, i.e. a spatial distribution of the syringe response. Dose data indicative of the optical response pattern is then recorded. The light source preferably includes plural longitudinally spaced light emitters. Each light emitter generates a light beam incident on the syringe. The optical response pattern is indicative of the interaction of the light beams with the syringe. Preferably, each of the light emitters is substantially aligned longitudinally with one of the detecting elements. If a control means in electrical communication with each of the light emitters is used to individually control each of the light emitters, a separate response pattern may be recorded for each emitter.

In an embodiment which does not require an internal light source, the holding means encloses the syringe only on one side. The holding means does not completely enclose the syringe on the side opposite the detector, so as to allow external light to be incident on the syringe. The response pattern detected by the detector is then dependent on the interaction between the external light and the syringe.

In one embodiment, the syringe includes a response-enhancing element comprising an optical marking. The optical response of the syringe depends on the interaction of incident light with the marking, and on the position of the marking. The position of the marking is indicative of the dose. The response-enhancing element may comprise a longitudinal element mechanically coupled to (e.g. on the surface of, or within) the syringe plunger. The longitudinal element is longitudinally marked by the marking. The marking may be a shape marking, or a color marking varying longitudinally in brightness and/or hue.

If the detector detects light transmitted or emitted by the syringe, the detector is situated opposite the light source relative to the syringe. If the detector detects light reflected by the syringe, the detector is situated adjacent the light source relative to the syringe (on the same side of the syringe).

A port connected to the recording means allows downloading dose data histories from the recording means to a host computer (storage and communications device). A display connected to the detector and/or recording means displays dose data including current doses and dose histories to the patient. Generally, the recording means may record any signal indicative of the optical response detected by the detector. For example, the recording means may record directly the optical response signal generated by the detector. Doses are then computed on a distinct computer after downloading of the recording means contents to the computer. Preferably, however, a computing means computes the dose data recorded by the recording means from the optical response by the detector.

Preferably, a housing encloses the light source, detector, recording means, and monitoring means. The holding means is mechanically coupled with the housing, and is preferably enclosed by the housing. The housing may be sufficiently compact to be hand-held and carried by a user, and may be battery-powered.

ii) Capacitance-based Measurement

An apparatus for capacitively measuring and electronically recording a dose delivered from a syringe includes: a holder for receiving and holding a syringe in a measurement position; a capacitive element coupled to the holder and enclosing the syringe such that a capacitive response of the capacitive element is indicative of the dose when the syringe is in the measurement position; a measuring device connected to the capacitive element for measuring capacitive responses of the capacitive element; and a recording device connected to the measuring device for recording a dose datum indicative of the capacitive response and thus indicative of the dose.

Preferably, the holder includes a well, the well laterally enclosing the syringe when the syringe is in the measurement position. The capacitive element is then coupled to the well such that at least one electrode of the capacitive element laterally encloses the syringe when the syringe is in the measurement position. In one embodiment, the capacitive element is defined between the liquid held in the syringe and an external electrode situated outside the syringe. A needle contact coupled to the holder is then used to establish electrical communication between the measuring device and the liquid, through the syringe needle, when the syringe is in the measurement position. In another embodiment, the capacitive element is defined between first and second electrically conducting longitudinal plates coupled to the holder, electrically insulated from each other, and situated opposite each other relative to the syringe.

In yet another embodiment, the capacitive element is situated entirely within the syringe. Two coaxial cylindrical electrodes, one near the inside surface of the syringe barrel and the other near the outside surface of the syringe plunger, are connected to input and output terminals on the outside of the syringe barrel. The housing includes a contact field coupled to the outside of the housing. The contact field includes an input contact for contacting the input terminal, and an output contact for contacting the output terminal. The input and output contacts are connected to the measuring device.

A housing encloses the measuring and recording devices, and preferably encloses and magnetically shields the capacitive element. The holder is mechanically coupled to the housing. The housing is sufficiently compact to be hand-held and carried by a user. The capacitive element preferably consists of a single capacitor, and the capacitive response preferably includes the capacitance of the capacitor. In an alternative embodiment, the capacitive element includes plural longitudinally-spaced capacitors, and the capacitive response includes a capacitive response pattern.

iii) Inductance-based Dose Measurement

An apparatus for inductively measuring and electronically recording a dose delivered using a syringe includes: a holder for receiving and holding a syringe in a measurement position; an inductive element coupled to the holder and enclosing the syringe such that an inductive response of the inductive element is indicative of the dose when the syringe is in the measurement position; a measuring device connected to the inductive element for measuring inductive responses of the inductive element; and a recording device connected to the measuring device for recording a dose datum indicative of the inductive response and thus indicative of the dose.

Preferably, the holder includes a well laterally enclosing the syringe when the syringe is in the measurement position. The inductor is then coupled to the well such that the inductor laterally encloses the syringe when the syringe is in the measurement position. It is preferred that the syringe includes an inductance-enhancing element whose position relative to the syringe barrel is indicative of the dose, and whose position determines the inductive response of the inductive element. The inductance-enhancing element preferably includes a ferromagnetic or ferromagnetic longitudinal plunger element embedded in a plastic shell to form the syringe plunger. The inductance-enhancing element preferably includes a ferrite strip, but may comprise a ferromagnetic core filling the plunger cross-section almost entirely, or a series of longitudinally spaced, stacked disks arranged within the plunger. Alternatively, a conventional syringe having a plunger consisting essentially of a plastic rod may be used.

A housing encloses the measuring and recording devices, and preferably encloses and magnetically shields the inductive element. The holder is mechanically coupled to the housing. The housing is sufficiently compact to be hand-held and carried by a user. The inductive element preferably consists of a single inductor, and the inductive response preferably includes the inductance of the inductor. In an alternative embodiment, the inductive element includes plural longitudinally spaced inductors, and the inductive response includes an inductive response pattern.

In one embodiment, the inductor is situated within the syringe barrel and is connected to input and output terminals on the outside of the syringe. The housing then includes a contact field coupled to the outside of the housing. The contact field includes an input contact for contacting the input terminal, and an output contact for contacting the output terminal.

For both inductive and capacitive measurement embodiments of the monitoring system, a port connected to the recording device may be used to download data stored in the recording device to an external storage or communication device, such as a host computer. Also connected to the recording device is a monitoring or testing device for testing a physical or physiological condition of the patient and for generating condition data representative of the physical or physiological condition. The recording device records the condition data. Preferably, the monitoring or testing device is a blood glucose meter and the physical or physiological condition is the patient's blood glucose level. A display connected to the measuring device is used to display recorded doses and blood glucose levels to the patient.

A computing device is connected to the recording device. The computing device computes dose data from dose measurement responses (capacitive, inductive, or optical) and stored calibration data, for storage in the recording device. Dose data preferably includes administered doses. The calibration data, stored in a calibration memory device, is indicative of the correspondence between dose measurement responses and dose data for the particular syringe used by the patient. The calibration data is generated by measuring dose measurement responses for the entire range of potential liquid quantities in the syringe, and recording the correspondence between liquid quantities and dose measurement responses.

BRIEF DESCRIPTION OF THE DRAWINGS

FIG. 5 is a script entry screen according to a preferred embodiment of the invention.

FIG. 6A is a listing of a sample script program according to a preferred embodiment of the invention.

FIG. 6B is a continuation of the listing of FIG. 6A.

FIG. 10 is a sample report displayed on a workstation of the system of FIG. 1.

FIG. 27A is a longitudinal sectional view of a syringe suitable for use with the apparatus of FIG. 24A.

FIG. 27B is a transverse sectional view of the syringe of FIG. 27A.

FIG. 28 is a longitudinal sectional view of an inductance-enhanced syringe of the invention.

FIG. 29A is a longitudinal section view of a multi-inductor element according to the invention.

FIG. 29B is a longitudinal section view of another multi-inductor element according to the invention.

FIG. 32B is a longitudinal sectional view of a syringe situated in a measurement position in a holder of the apparatus of FIG. 32A, illustrating a preferred light source and detector arrangement.

FIG. 32C shows a detail of FIG. 32B, including the plunger-liquid interface within the syringe.

FIG. 32D shows an alternative light source and detector arrangement in a view similar to that of FIG. 32C, according to the invention.

FIG. 33A shows an apparatus which does not require an internal light source, according to another embodiment of the invention.

FIG. 34 shows a perspective view of a drug delivery measurement apparatus and a syringe adapted for use with the apparatus, according to another embodiment of the invention.

DETAILED DESCRIPTION

The invention presents a system and method for remotely monitoring individuals, for communicating information to the individuals, and for receiving data from an individual at a remote location. In a preferred embodiment of the invention, the individuals are patients and the system is used to collect data relating to the health status or medical treatment of the patients. However, it is to be understood that the invention is not limited to remote monitoring of patients or patient-related activities. The system and method of the invention may be used for any type of remote monitoring application. The invention may also be implemented as an automated messaging system for communicating information to individuals, as will be discussed in an alternative embodiment below.

A system and method for remote interactive communication and remote monitoring of individuals will first be described with reference to FIGS. 1–19. Thereafter, a system for patient monitoring and drug delivery measurement, including a drug delivery measurement apparatus for use in conjunction with the interactive communication and remote monitoring system, will be described with reference to FIGS. 20A–34.

Figure 1:
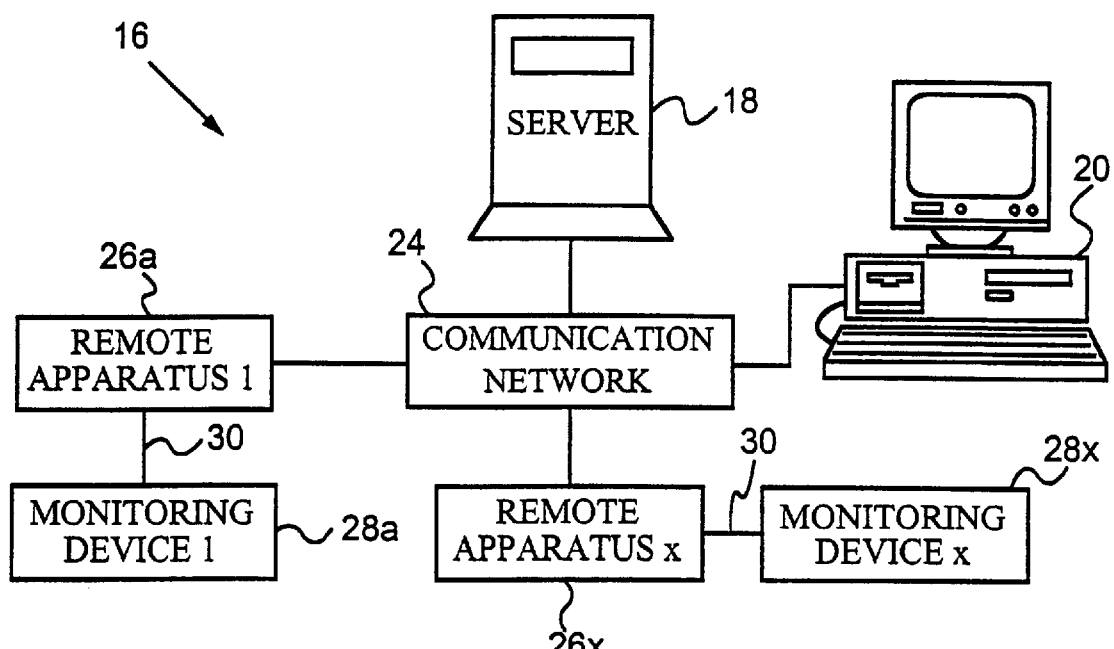
FIG. 1 is a block diagram of a networked system according to one embodiment of the invention.

A preferred embodiment of the invention is illustrated in FIGS. 1–12. Referring to FIG. 1, a networked system 16 includes a server 18 and a workstation 20 connected to server 18 through a communication network 24. Server 18 is preferably a worldwide web server and communication network 24 is preferably the Internet. It will be apparent to one skilled in the art that server 18 may comprise a single stand-alone computer or multiple computers distributed throughout a network. Workstation 20 is preferably a personal computer, remote terminal, or web TV unit connected to server 18 via the Internet. Workstation 20 functions as a remote interface for entering in server 18 messages and queries to be communicated to the patients.

System 16 also includes a plurality of remotely programmable apparatuses, schematically represented in FIG. 1 as 26a and 26x for monitoring a corresponding plurality of patients. Each remotely programmable apparatus 26a–x is designed to interact with a patient in accordance with script programs received from server 18. Each remotely programmable apparatus 26a–x is in communication with server 18 through communication network 24, preferably the Internet. Alternatively, each apparatus, e.g., 26a, may be placed in communication with server 18 via wireless communication networks, cellular networks, telephone networks, or any other network which allows each remotely programmable apparatus 26a to exchange data with server 18. For clarity of illustration, only two remotely programmable apparatus 26aes are shown in FIG. 1. However, it is to be understood that system 16 may include any number of remotely programmable apparatus 26a–x for monitoring any number of patients.

Each patient to be monitored may be provided with a monitoring device 28a–x, designed to provide measurements of a physiological condition of the patient, to record the physiological condition measurements, and to transmit the measurements to the patient's remotely programmable apparatus 26a–x, e.g., through a standard connection cable 30. Examples of suitable types of monitoring devices include blood glucose meters, respiratory flow meters, blood pressure cuffs, electronic weight scales, and pulse rate monitors. Such monitoring devices are well known in the art. The specific type of monitoring device provided to each patient is dependent upon the patient's disease. For example, diabetes patients are provided with a blood glucose meters for measuring blood glucose concentrations, asthma patients are provided with respiratory flow meters for measuring peak flow rates, obesity patients are provided with weight scales, etc.

Figure 2:
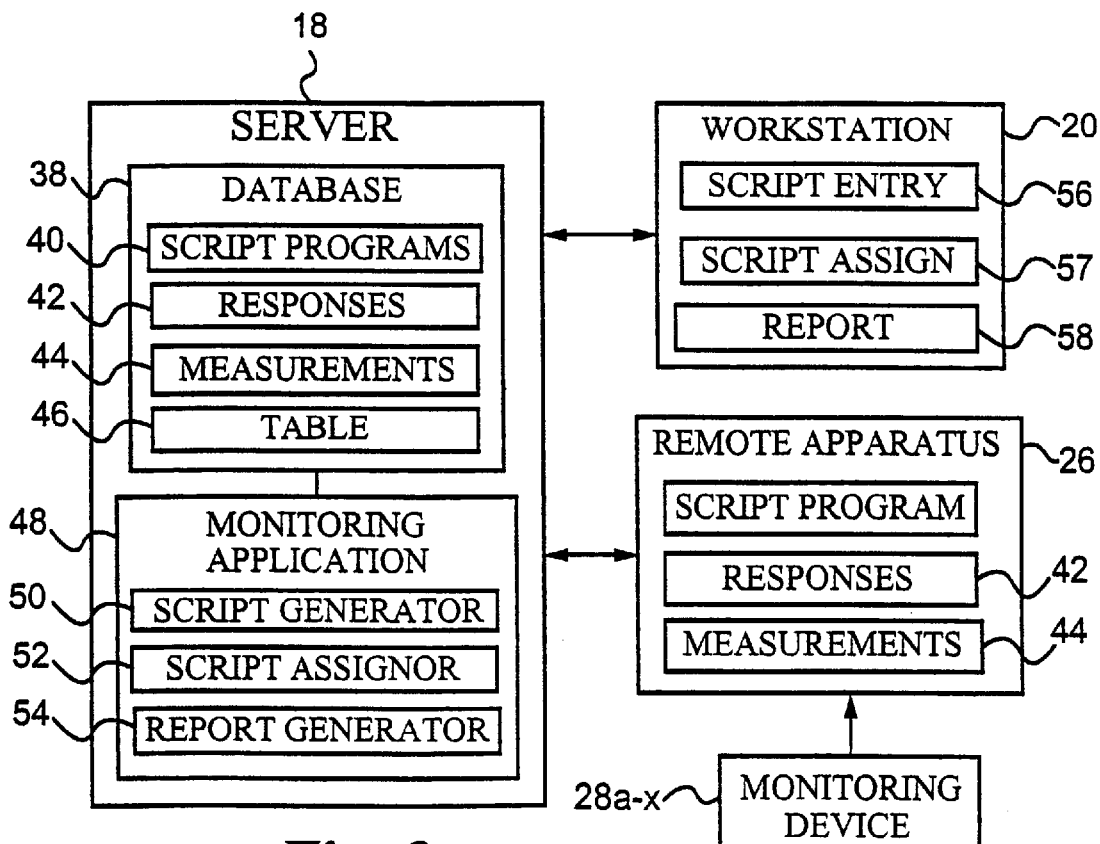
FIG. 2 is a block diagram illustrating the interaction of the components of the system of FIG. 1.

FIG. 2 shows server 18, workstation 20, and remotely programmable apparatus 26a–x in greater detail. Server 18 includes a database 38 for storing script programs 40. The script programs are executed by each remotely programmable apparatus to communicate queries and messages to a patient, receive responses 42 to the queries, collect monitoring device measurements 44, and transmit responses 42 and measurements 44 to server 18. Database 38 is designed to store the responses 42 and measurements 44. Database 38 further includes a look-up table 46. Table 46 contains a list of the patients to be monitored, and for each patient, a unique patient identification code and a respective pointer to the script program assigned to the patient. Each remotely programmable apparatus 26a–x is designed to execute assigned script programs which it receives from server 18.

Figure 3:
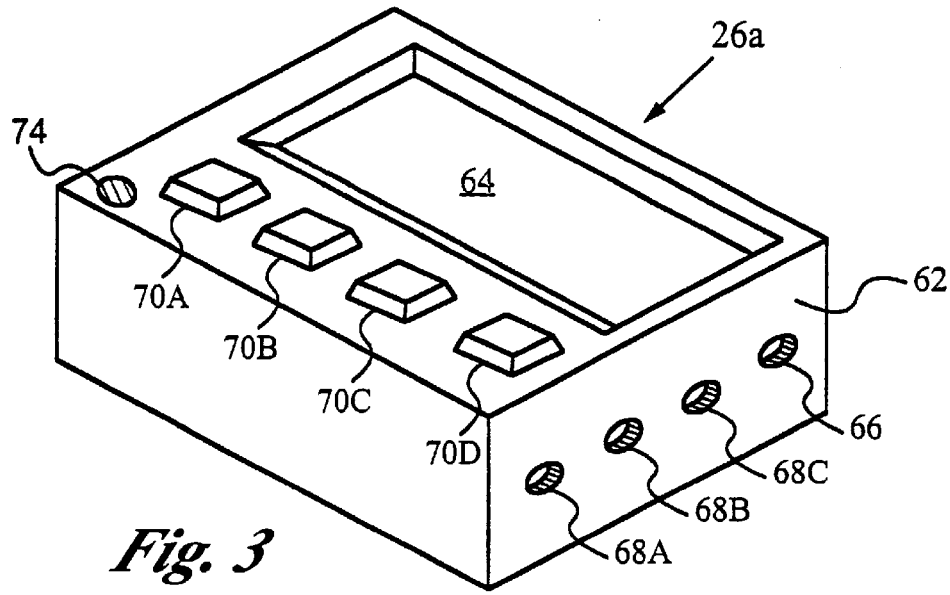
FIG. 3 is a perspective view of a remotely programmable apparatus of the system of FIG. 1.
Figure 4:
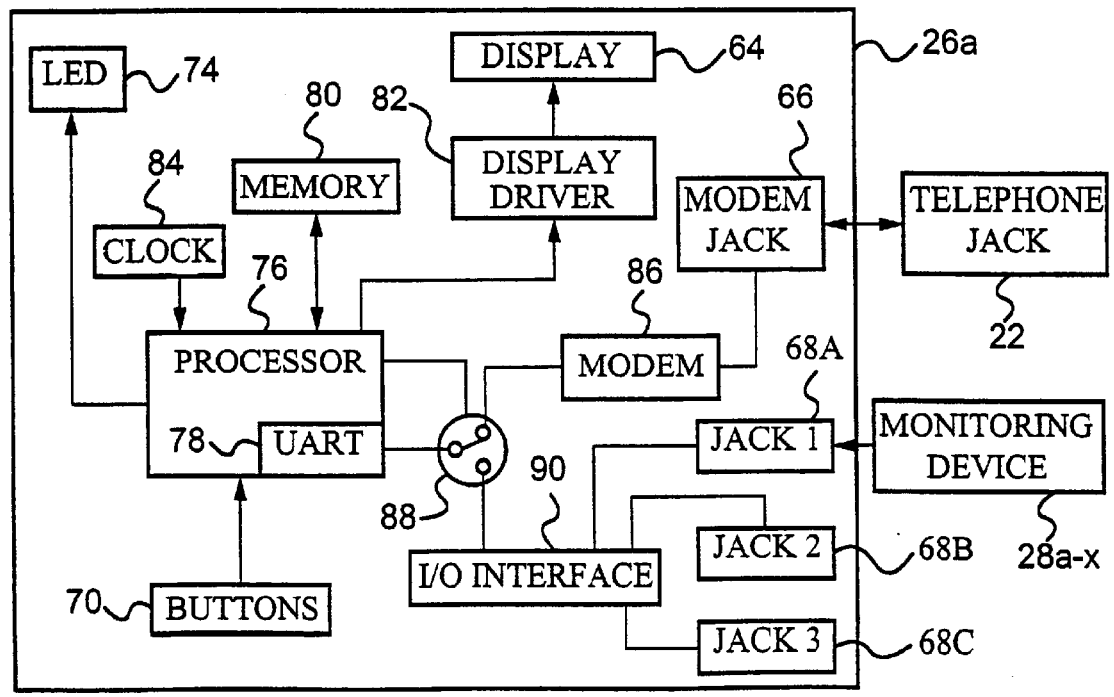
FIG. 4 is a block diagram illustrating the components of the remotely programmable apparatus of FIG. 3.

FIGS. 3–4 show the structure of each remotely programmable apparatus according to a preferred embodiment. For clarity, only remotely programmable apparatus 26a is shown in FIGS. 3–4, since each remotely programmable apparatus 26a–x has substantially the same structure as remotely programmable apparatus 26a. Referring to FIG. 3, remotely programmable apparatus 26a includes a housing 62. Housing 62 is sufficiently compact to enable apparatus 26a to be hand-held and carried by a patient. Remotely programmable apparatus 26a also includes a display 64 for displaying queries and prompts to the patient. In a preferred embodiment, display 64 is a liquid crystal display (LCD).

Four user input buttons 70A, 70B, 70C, and 70D are located adjacent display 64. User input buttons 70A–C are for entering in remotely programmable apparatus 26a responses to the queries and prompts. In a preferred embodiment, user input buttons 70A–C are momentary contact push buttons. In alternative embodiments, user input buttons 70A–C may be replaced by switches, keys, a touch sensitive display screen, or any other data input device.

Three monitoring device jacks 68A, 68B, and 68C are located on a surface of housing 62. The device jacks are for connecting remotely programmable apparatus 26a to a number of monitoring devices, such as blood glucose meters, respiratory flow meters, or blood pressure cuffs, through respective connection cables (not shown). Apparatus 26a also includes a modem jack 66 for connecting apparatus 26a to a telephone jack through a standard connection cord (not shown). Apparatus 26a further includes a visual indicator, such as a light emitting diode (LED) 74. LED 74 is for visually notifying the patient that he or she has unanswered queries stored in remotely programmable apparatus 26a.

FIG. 4 is a schematic block diagram illustrating the components of apparatus 26a in greater detail. Apparatus 26a includes a microprocessor 76 and a memory 80 connected to microprocessor 76. Memory 80 is preferably a non-volatile memory, such as a serial EEPROM. Memory 80 stores script programs received from the server, measurements received from monitoring device 28, responses to queries, and the patient's unique identification code. Microprocessor 76 also includes built-in read only memory (ROM) which stores firmware for controlling the operation of apparatus 26a. The firmware includes a script interpreter used by microprocessor 76 to execute the script programs. The script interpreter interprets script commands which are executed by microprocessor 76. Specific techniques for interpreting and executing script commands in this manner are well known in the art.

Microprocessor 76 is preferably connected to memory 80 using a standard two-wire I$^2$C interface. Microprocessor 76 is also connected to user input buttons 70, LED 74, a clock 84, and a display driver 82. Clock 84 indicates the current date and time to microprocessor 76. For clarity of illustration, clock 84 is shown as a separate component, but is preferably built into microprocessor 76. Display driver 82 operates under the control of microprocessor 76 to display information on display 64. Microprocessor 76 is preferably a PIC 16C65 processor which includes a universal asynchronous receiver transmitter (UART) 78. UART 78 is for communicating with a modem 86 and a device interface 90. A CMOS switch 88 under the control of microprocessor 76 alternately connects modem 86 and interface 90 to UART 78.

Modem 86 is connected to a telephone jack 22 through modem jack 66. Modem 86 is for exchanging data with server 18 through communication network 24. The data includes script programs which are received from server 18 as well as responses to queries, device measurements, script identification codes, and the patient's unique identification code which modem 86 transmits to server 18. Modem 86 is preferably a complete 28.8 K modem commercially available from Cermetek, although any suitable modem may be used.

Device interface 90 is connected to device jacks 68A, 68B, and 68C. Device interface 90 is for interfacing with a number of monitoring devices, such as blood glucose meters, respiratory flow meters, blood pressure cuffs, weight scales, or pulse rate monitors, through device jacks 68A–C. Device interface 90 operates under the control of microprocessor 76 to collect measurements from the monitoring devices and to output the measurements to microprocessor 76 for storage in memory 80. In a preferred embodiment, interface 90 is a standard RS232 interface. For simplicity of illustration, only one device interface is shown in FIG. 4. However, in alternative embodiments, remotely programmable apparatus 26a may include multiple device interfaces to accommodate monitoring devices which have different connection standards.

Referring again to FIG. 2, server 18 includes a monitoring application 48. Monitoring application 48 is a controlling software application executed by server 18 to perform the various functions described below. Application 48 includes a script generator 50, a script assignor 52, and a report generator 54. Script generator 50 is designed to generate script programs 40 from script information entered through workstation 20. The script information is entered through a script entry screen 56. In a preferred embodiment, script entry screen 56 is implemented as a web page on server 18. Workstation 20 includes a web browser for accessing the web page to enter the script information.

FIG. 5 illustrates script entry screen 56 as it appears on workstation 20. Screen 56 includes a script name field 92 for specifying the name of a script program to be generated. Screen 56 also includes entry fields 94 for entering a set of queries to be answered by a patient. Each entry field 94 has corresponding response choice fields 96 for entering response choices for the query. Screen 56 further includes check boxes 98 for selecting a desired monitoring device from which to collect measurements, such as a blood glucose meter, respiratory flow meter, or blood pressure cuff.

Screen 56 additionally includes a connection time field 100 for specifying a prescribed connection time at which each remotely programmable apparatus 26a–x executing the script is to establish a subsequent communication link to server 18. The connection time is preferably selected to be the time at which communication rates are the lowest, such as 3:00 AM. Screen 56 also includes a CREATE SCRIPT button 102 for instructing the script generator to generate a script program from the information entered in screen 56. Screen 56 further includes a CANCEL button 104 for canceling the information entered in screen 56.

In a preferred embodiment, each script program created by the script generator conforms to the standard file format used on UNIX systems. In the standard file format, each command is listed in the upper case and followed by a colon. Every line in the script program is terminated by a linefeed character {LF}, and only one command is placed on each line. The last character in the script program is a UNIX end of file character {EOF}. Table 1 shows an exemplary listing of script commands used in a preferred embodiment of the invention.

TABLE 1

SCRIPT COMMANDS

| Command | Description |
| --- | --- |
| CLS: {LF} | Clear the display. |
| ZAP: {LF} | Erase from memory the last set of query responses recorded. |
| LED: b{LF} | Turn the LED on or off, where b is a binary digit of 0 or 1. An argument of 1 turns on the LED, and an argument of 0 turns off the LED. |
| DISPLAY: {chars}{LF} | Display the text following the DISPLAY command. |
| INPUT: mmmm{LF} | Record a button press. The m's represent a button mask pattern for each of the four input buttons. Each m contains an "X" for disallowed buttons or an "O"for allowed buttons. For example, INPUT: OXOX{LF} allows the user to press either button #1 or #3. |
| WAIT: {LF} | Wait for any one button to be pressed, then continue executing the script program. |
| COLLECT: device{LF} | Collect measurements from the monitoring device specified in the COLLECT command. The user is preferably prompted to connect the specified monitoring device to the apparatus and press a button to continue. |
| NUMBER: aaaa{LF} | Assign a script identification code to the script program. The script identification code from the most recently executed NUMBER statement is subsequently transmitted to the server along with the query responses and device measurements. The script identification code identifies to the server which script program was most recently executed by the remote apparatus. |
| DELAY: t{LF} | Wait until time t specified in the DELAY command, usually the prescribed connection time. |
| CONNECT: {LF} | Perform a connection routine to establish a communication link to the server, transmit the patient identification code, query responses, device measurements, and script identification code to the server, and receive and store a new script program. When the server instructs the apparatus to disconnect, the script interpreter is restarted, allowing the new script program to execute. |

The script commands illustrated in Table 1 are representative of the preferred embodiment and are not intended to limit the scope of the invention. After consideration of the ensuing description, it will be apparent to one skilled in the art many other suitable scripting languages and sets of script commands may be used to implement the invention.

Script generator 50 preferably stores a script program template which it uses to create each script program. To generate a script program, script generator 50 inserts into the template the script information entered in screen 56. For example, FIGS. 6A–6B illustrate a sample script program created by script generator 50 from the script information shown in FIG. 5.

The script program includes display commands to display the queries and response choices entered in fields 94 and 96, respectively. The script program also includes input commands to receive responses to the queries. The script program further includes a collect command to collect device measurements from the monitoring device 28*a–x* specified in check boxes 98. The script program also includes commands to establish a subsequent communication link to server 18 at the connection time specified in field 100. The steps included in the script program are also shown in the flow chart of FIGS. 12A–12B and will be discussed in the operation section below.

Referring again to FIG. 2, script assignor 52 is for assigning script programs 40 to the patients. Script programs 40 are assigned in accordance with script assignment information entered through workstation 20. The script assignment information is entered through a script assignment screen 57, which is preferably implemented as a web page on server 18.

Figure 7:
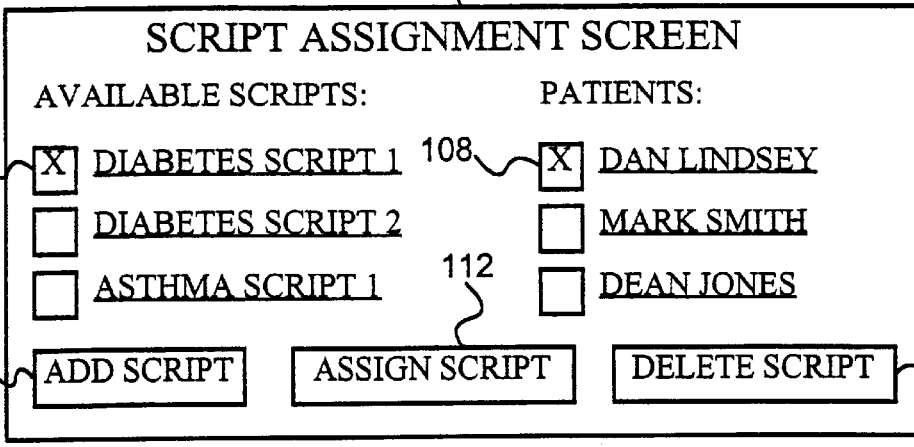
FIG. 7 is a script assignment screen according to a preferred embodiment of the invention.

FIG. 7 illustrates a sample script assignment screen 57 as it appears on workstation 20. Screen 57 includes check boxes 106 for selecting a script program to be assigned and check boxes 108 for selecting the patients to whom the script program is to be assigned. Screen 57 also includes an ASSIGN SCRIPT button 112 for entering the assignments.

When button 112 is activated, the script assignor creates and stores for each patient selected in check boxes 108 a respective pointer to the script program selected in check boxes 106. Each pointer is stored in the patient look-up table of the database. Screen 57 further includes an ADD SCRIPT button 110 for accessing the script entry screen and a DELETE SCRIPT button 114 for deleting a script program.

Referring again to FIG. 2, report generator 54 is designed to generate a patient report 58 from the responses and device measurements received in server 18. Patient report 58 is displayed on workstation 20. FIG. 10 shows a sample patient report 58 produced by report generator 54 for a selected patient. Patient report 58 includes a graph 116 of the device measurements received from the patient, as well as a listing of responses 42 received from the patient. Specific techniques for writing a report generator program to display data in this manner are well known in the art.

The operation of a preferred embodiment is illustrated in FIGS. 1–12. FIG. 11A is a flow chart illustrating steps included in the monitoring application executed by server 18. FIG. 11B is a continuation of the flow chart of FIG. 11A. In step 202, server 18 determines if new script information has been entered through script entry screen 56. If new script information has not been entered, server 18 proceeds to step 206. If new script information has been entered, server 18 proceeds to step 204.

As shown in FIG. 5, the script information includes a set of queries, and for each of the queries, corresponding response choices. The script information also includes a selected monitoring device type from which to collect device measurements. The script information further includes a prescribed connection time for each remotely programmable apparatus 26*a* to establish a subsequent communication link to server 18. The script information is generally entered in server 18 by a healthcare provider, such as the patients' physician or case manager. Of course, any person desiring to communicate with the patients may also be granted access to server 18 to create and assign script programs. Further, it is to be understood that system 16 may include any number of remote interfaces for entering script generation and script assignment information in server 18.

In step 204, script generator 50 generates a script program from the information entered in screen 56. The script program is stored in database 38. Steps 202 and 204 are preferably repeated to generate multiple script programs, e.g. a script program for diabetes patients, a script program for asthma patients, etc. Each script program corresponds to a respective one of the sets of queries entered through script entry screen 56. Following step 204, server 18 proceeds to step 206.

In step 206, server 18 determines if new script assignment information has been entered through assignment screen 57. If new script assignment information has not been entered, server 18 proceeds to step 210. If new script assignment information has been entered, server 18 proceeds to step 208. As shown in FIG. 7, the script programs are assigned to each patient by selecting a script program through check boxes 106, selecting the patients to whom the selected script program is to be assigned through check boxes 108, and pressing the ASSIGN SCRIPT button 112. When button 112 is pressed, script assignor 52 creates for each patient selected in check boxes 108 a respective pointer to the script program selected in check boxes 106. In step 208, each pointer is stored in look-up table 46 of database 38. Following step 208, server 18 proceeds to step 210.

In step 210, server 18 determines if any of the remotely programmable apparatus 26aes are remotely connected to server 18. Each patient to be monitored is preferably provided with his or her own remotely programmable apparatus 26a–x which has the patient's unique identification code stored therein. Each patient is thus uniquely associated with a respective one of apparatus 26a–x. If none of remotely programmable apparatus 26a–x is connected, server 18 proceeds to step 220.

If an apparatus 26a–x is connected, server 18 receives from that remotely programmable apparatus the patient's unique identification code in step 212. In step 214, server 18 receives from the remotely programmable apparatus 26a the query responses 42, device measurements 44, and script identification code recorded during execution of a previously assigned script program. The script identification code identifies to server 18 which script program was executed by the apparatus 26a–x to record the query responses and device measurements. The responses, device measurements, and script identification code are stored in database 38.

In step 216, server 18 uses the patient identification code to retrieve from table 46 the pointer to the script program assigned to the patient. Server 18 then retrieves the assigned script program from database 38. In step 218, server 18 transmits the assigned script program to the patient's remotely programmable apparatus 26a–x through communication network 24. Following step 218, server 18 proceeds to step 220.

In step 220, server 18 determines if a patient report request has been received from workstation 20. If no report request has been received, server 18 returns to step 202. If a report request has been received for a selected patient, server 18 retrieves from database 38 the measurements and query responses last received from the patient, step 222. In step 224, server 18 generates and displays patient report 58 on workstation 20. As shown in FIG. 10, report 58 includes the device measurements and query responses last received from the patient. Following step 224, server 18 returns to step 202.

Figure 12A:
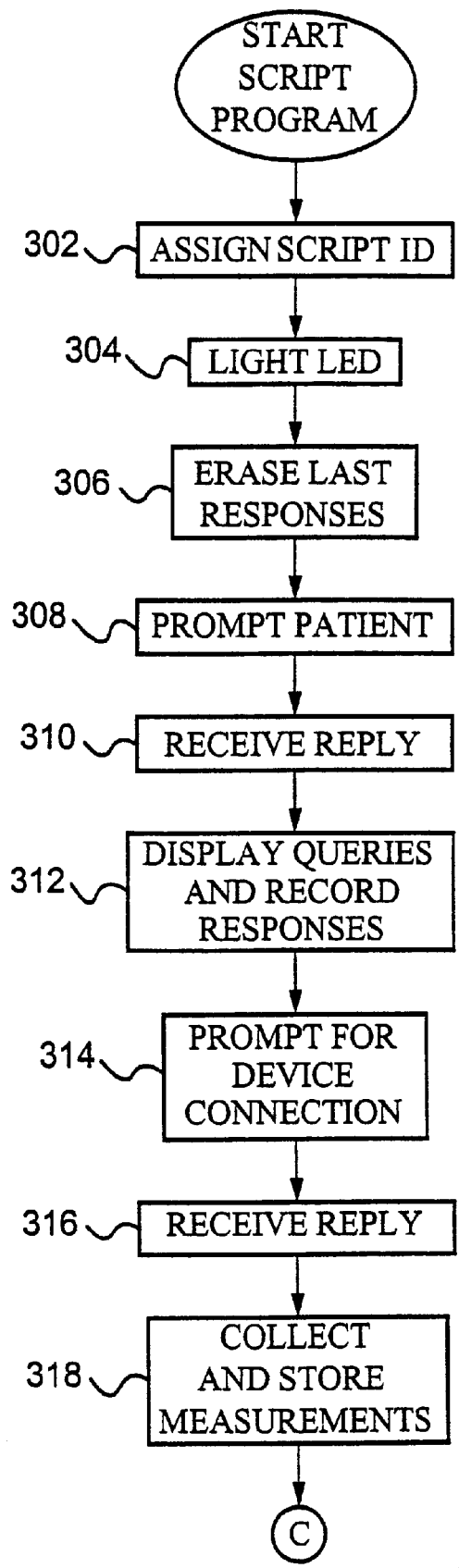
FIG. 12A is a flow chart illustrating the steps included in the script program of FIGS. 6A–6B.
Figure 12B:
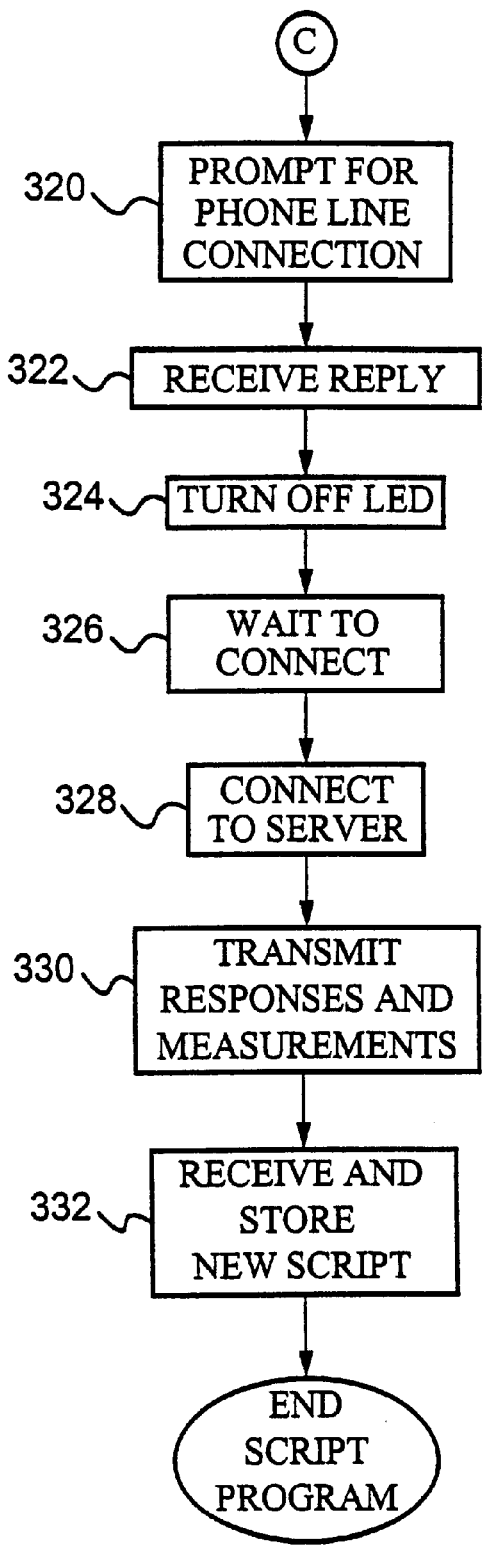
FIG. 12B is a continuation of the flow chart of FIG. 12A.

FIGS. 12A–12B illustrate the steps included in the script program executed by remotely programmable apparatus, e.g., 26a. Before the script program is received, remotely programmable apparatus 26a is initially programmed with the patient's unique identification code and the script interpreter used by microprocessor 76 to execute the script program. The initial programming may be achieved during manufacture of apparatus 26a or during an initial connection to server 18. Following initial programming, remotely programmable apparatus 26a receives from server 18 the script program assigned to the patient associated with remotely programmable apparatus 26a. The script program is received by modem 86 through a first communication link and stored in memory 80.

In step 302, microprocessor 76 assigns a script identification code to the script program and stores the script identification code in memory 80. The script identification code is subsequently transmitted to server 18 along with the query responses and device measurements to identify to server 18 which script program was most recently executed by apparatus 26a. In step 304, microprocessor 76 lights LED 74 to notify the patient that he or she has unanswered queries stored in remotely programmable apparatus 26a. LED 74 preferably remains lit until the queries are answered by the patient. In step 306, microprocessor 76 erases from memory 80 the last set of query responses recorded. In step 308, microprocessor 76 prompts the patient by displaying on display 64 "ANSWER QUERIES NOW? PRESS ANY BUTTON TO START". In step 310, microprocessor 76 waits until a reply to the prompt is received from the patient. When a reply is received, microprocessor 76 proceeds to step 312. In step 312, microprocessor 76 executes successive display and input commands to display the queries and response choices on display 64 and to receive responses to the queries.

Figure 8:
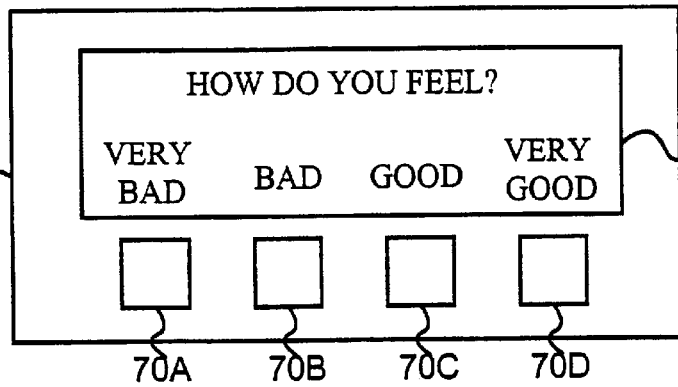
FIG. 8 is a sample query appearing on a display of the apparatus of FIG. 3.

FIG. 8 illustrates a sample query and its corresponding response choices as they appear on display 64. The response choices are positioned on display 64 such that each response choice is located proximate a respective one of the input buttons 70A–D. In the preferred embodiment, each response choice is displayed immediately above a respective input button 70A–D. The patient presses the button (70A–D) corresponding to his or her response. Microprocessor 76 stores each response in memory 80.

Figure 9:
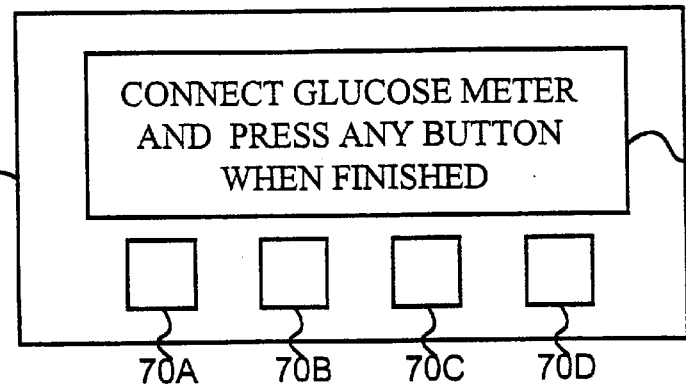
FIG. 9 is a sample prompt appearing on the display of the apparatus of FIG. 3.
Figure 11A:
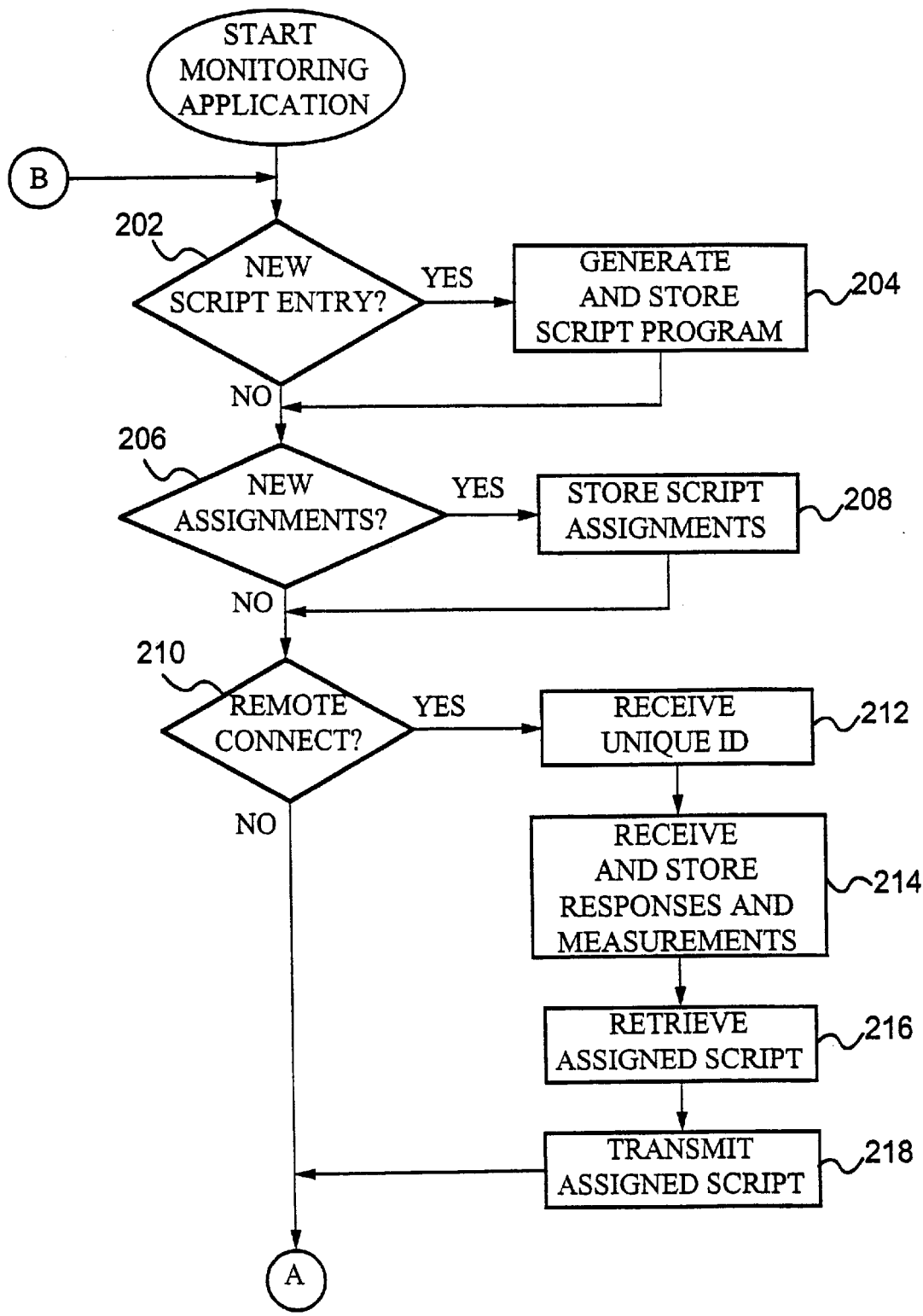
FIG. 11A is a flow chart illustrating the steps included in a monitoring application executed by the server of FIG. 1 according to a preferred embodiment of the invention.
Figure 11B:
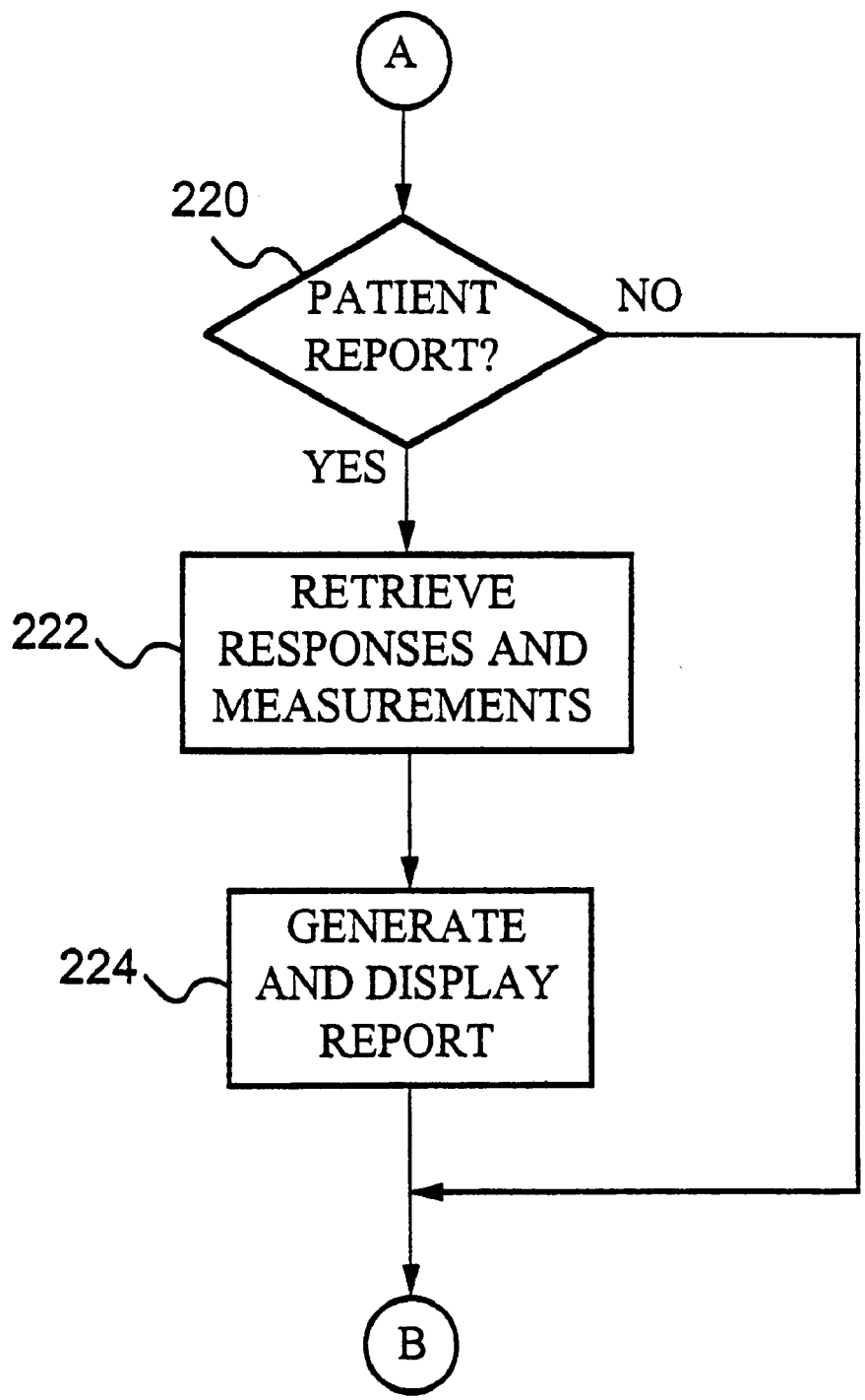
FIG. 11B is a continuation of the flow chart of FIG. 11A.

In steps 314–318, microprocessor 76 executes commands to collect device measurements from a selected monitoring device 28a–x. The script program specifies the selected monitoring device 28a–x from which to collect the measurements. In step 314, microprocessor 76 prompts the patient to connect a selected monitoring device 28a–x, for example a blood glucose meter, to one of device jacks 68A–C. A sample prompt is shown in FIG. 9. In step 316, microprocessor 76 waits until a reply to the prompt is received from the patient. When a reply is received, microprocessor 76 proceeds to step 318. Microprocessor 76 also connects UART 78 to interface 90 through switch 88. In step 318, microprocessor 76 collects the device measurements from monitoring device 28a–x through interface 90. The measurements are stored in memory 80.

In step 320, microprocessor 76 prompts the patient to connect remotely programmable apparatus 26a to telephone jack 22 so that remotely programmable apparatus 26a may connect to server 18 at the prescribed connection time. In step 322, microprocessor 76 waits until a reply to the prompt is received from the patient. When a reply is received, microprocessor 76 turns off LED 74 in step 324. In step 326, microprocessor 76 waits until it is time to connect to server 18. Microprocessor 76 compares the connection time specified in the script program to the current time output by clock 84. When it is time to connect, microprocessor 76 connects UART 78 to modem 86 through switch 88.

In step 328, microprocessor 76 establishes a subsequent communication link between apparatus 26a and server 18 through modem 86 and communication network 24. If the connection fails for any reason, microprocessor 76 repeats step 328 to get a successful connection. In step 330, microprocessor 76 transmits the device measurements, query responses, script identification code, and patient identification code stored in memory 80 to server 18 through the subsequent communication link. In step 332, microprocessor 76 receive s through modem 86 a new script program from server 18. The new script program is stored in memory 80 for subsequent execution by microprocessor 76. Following step 332, the script program ends.

One advantage of the monitoring system 16 of the present invention is that it allows each patient to select a convenient time to respond to the queries, so that the monitoring system is not intrusive to the patient's schedule. A second advantage of monitoring system 16 is that it incurs very low communications charges because each remote apparatus 26a–x connects to server 18 at times when communication rates are lowest. Moreover, the cost to manufacture each remote apparatus 26a–x is very low compared to personal computers or internet terminals.

A third advantage of the monitoring system is that it allows each apparatus 26a–x to be programmed remotely through script programs. Patient surveys, connection times, display prompts, selected monitoring devices, patient customization, and other operational details of each remotely programmable apparatus 26a–x may be easily changed by transmitting a new script program to the apparatus 26a–x. Moreover, each script program may be easily created and assigned by remotely accessing server 18 through the Internet. Thus, the invention provides a powerful, convenient, and inexpensive system for remotely monitoring a large number of patients.

Figure 13:
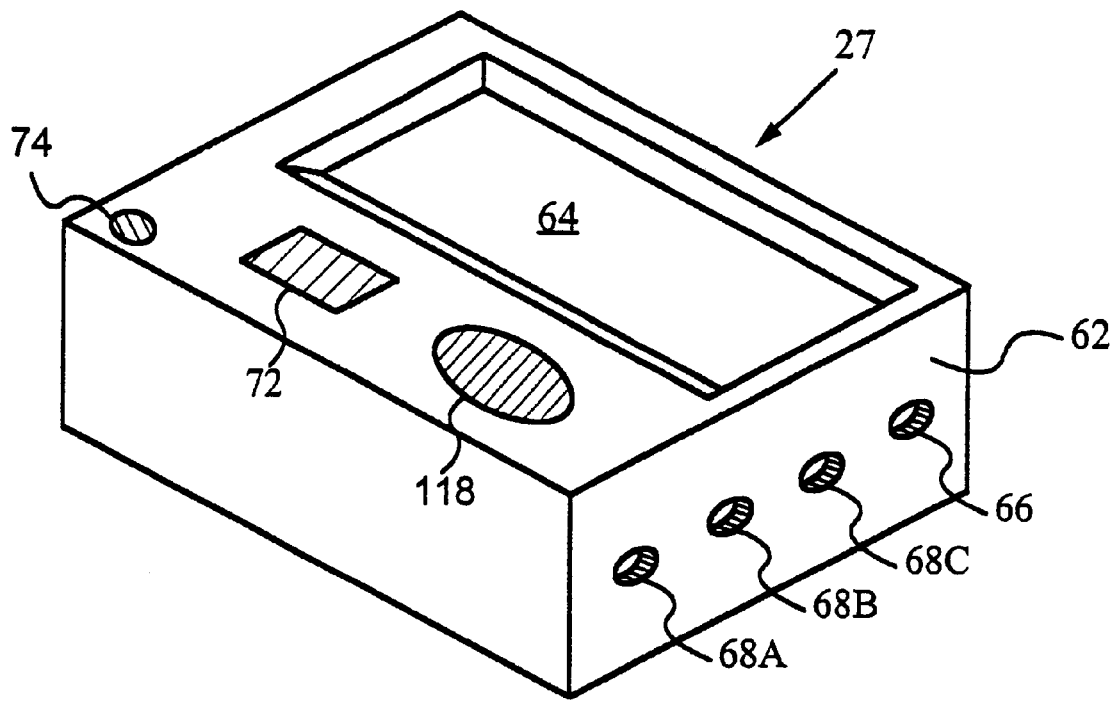
FIG. 13 is a perspective view of a remotely programmable apparatus according to a second embodiment of the invention.
Figure 14:
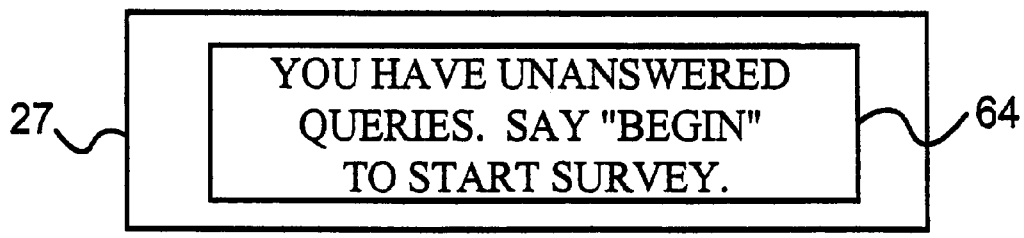
FIG. 14 is a sample prompt appearing on a display of the apparatus of FIG. 13.
Figure 15:
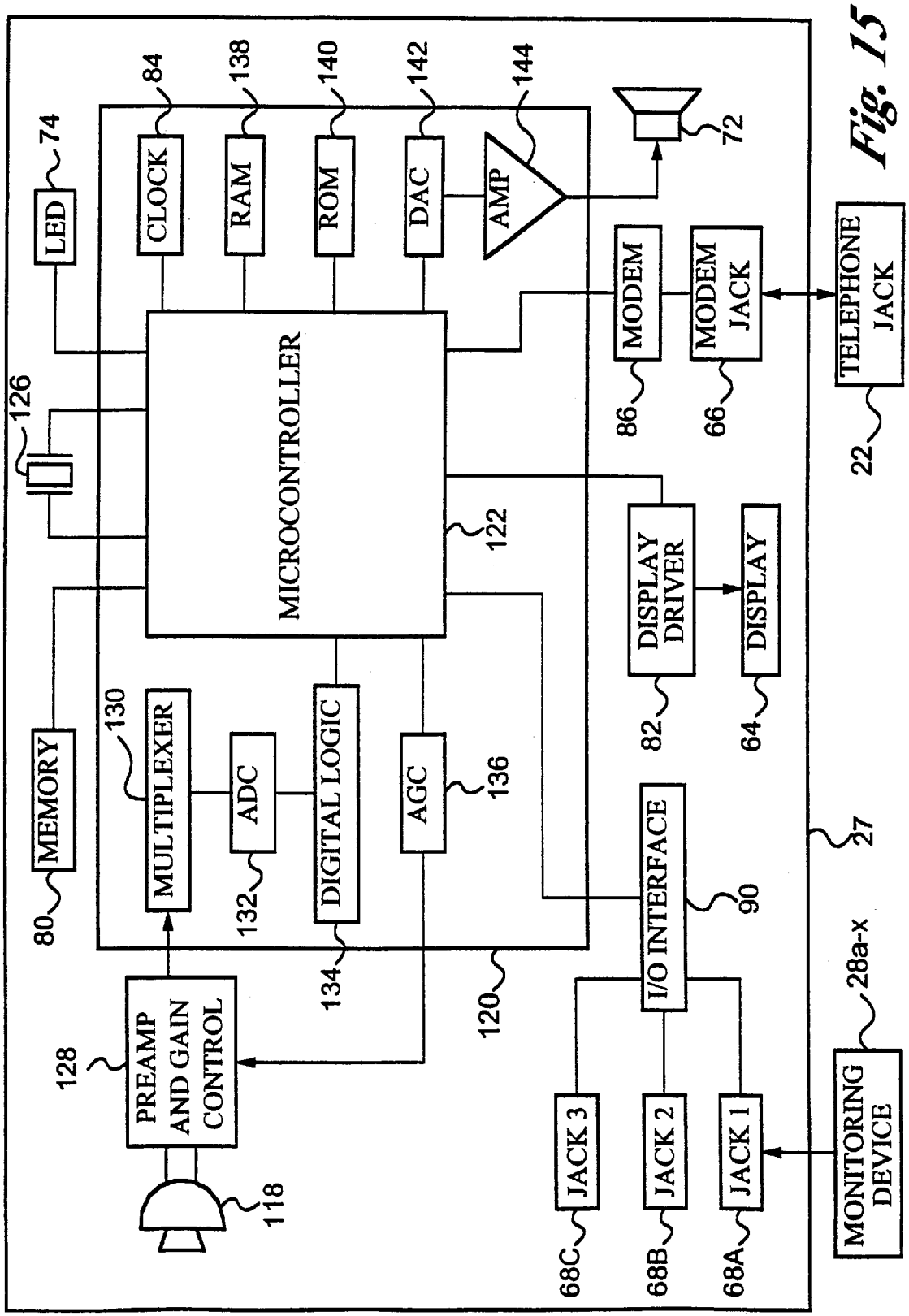
FIG. 15 is a block diagram illustrating the components of the apparatus of FIG. 13.

FIGS. 13–15 illustrate a second embodiment of the invention in which each remotely programmable apparatus has speech recognition and speech synthesis functionality. FIG. 13 shows a perspective view of a remotely programmable apparatus 27 according to the second embodiment. Apparatus 27 includes a speaker 72 for audibly communicating queries and prompts to the patient. Apparatus 27 also includes a microphone 118 for receiving spoken responses to the queries and prompts. Apparatus 27 may optionally include a display 64 for displaying prompts to the patient, as shown in FIG. 14.

FIG. 15 is a schematic block diagram illustrating the components of remotely programmable apparatus 27 in greater detail. Apparatus 27 is similar in design to remotely programmable apparatus 26a of the preferred embodiment, except that remotely programmable apparatus 27 includes an audio processor chip 120 in place of microprocessor 76. Audio processor chip 120 is can be an RSC-164 chip, such as is commercially available from Sensory Circuits Inc., San Jose, Calif.

Audio processor chip 120 has a microcontroller 122 for executing script programs received from server 18. A memory 80 is connected to microcontroller 122. Memory 80 stores the script programs and a script interpreter used by microcontroller 122 to execute the script programs. Memory 80 also stores measurements received from monitoring device 28, responses to the queries, script identification codes, and the patient's unique identification code.

Audio processor chip 120 also has built in speech synthesis functionality for synthesizing queries and prompts to a patient through speaker 72. For speech synthesis, chip 120 includes a digital to analog converter (DAC) 142 and an amplifier 144. DAC 142 and amplifier 144 drive speaker 72 under the control of microcontroller 122.

Audio processor chip 120 further has built in speech recognition functionality for recognizing responses spoken into microphone 118. Audio signals received through microphone 118 are converted to electrical signals and sent to a preamp and gain control circuit 128. Preamp and gain control circuit 128 is controlled by an automatic gain control circuit 136, which is in turn controlled by microcontroller 122. After being amplified by preamp 128, the electrical signals enter chip 120 and pass through a multiplexer 130 and an analog to digital converter (ADC) 132. The resulting digital signals pass through a digital logic circuit 134 and enter microcontroller 122 for speech recognition.

Audio processor chip 120 also includes a RAM 138 for short term memory storage and a ROM 140 which stores programs executed by microcontroller 122 to perform speech recognition and speech synthesis. Chip 120 operates at a clock speed determined by a crystal 126. Chip 120 also includes a clock 84 which provides the current date and time to microcontroller 122. As in a preferred embodiment, apparatus 27 includes an LED 74, display driver 82, modem 86, and device interface 90, all of which are connected to microcontroller 122.

The operation of the second embodiment is similar to the operation of the preferred embodiment except that queries, response choices, and prompts are audibly communicated to the patient through speaker 72 rather than being displayed to the patient on display 64. The operation of the second embodiment also differs from the operation of the preferred embodiment in that responses to the queries and prompts are received through microphone 118 rather than through user input buttons 76A–D.

The script programs of the second embodiment are similar to the script program shown in FIGS. 6A–6B, except that each display command is replaced by a speech synthesis command and each input command is replaced by a speech recognition command. The speech synthesis commands are executed by microcontroller 122 to synthesize the queries, response choices, and prompts through speaker 72. The speech recognition commands are executed by microcontroller 122 to recognize responses spoken into microphone 118.

For example, to ask the patient how he or she feels and record a response, microcontroller 122 first executes a speech synthesis command to synthesize through speaker 72 "How do you feel? Please answer with one of the following responses: very bad, bad, good, or very good." Next, microcontroller 118 executes a speech recognition command to recognize the response spoken into microphone 118. The recognized response is stored in memory 80 and subsequently transmitted to server 18. Other than the differences described, the operation and advantages of the second embodiment are the same as the operation and advantages of the preferred embodiment described above.

Although the first and second embodiments focus on querying individuals and collecting responses to the queries, the system of the invention is not limited to querying applications. The system may also be used simply to communicate messages to the individuals. FIGS. 16–19 illustrate a third embodiment in which the system is used to perform this automated messaging function. In the third embodiment, each script program contains a set of statements to be communicated to an individual rather than a set of queries to be answered by the individual. Of course, it will be apparent to one skilled in the art that the script programs may optionally include both queries and statements.

Figure 16:
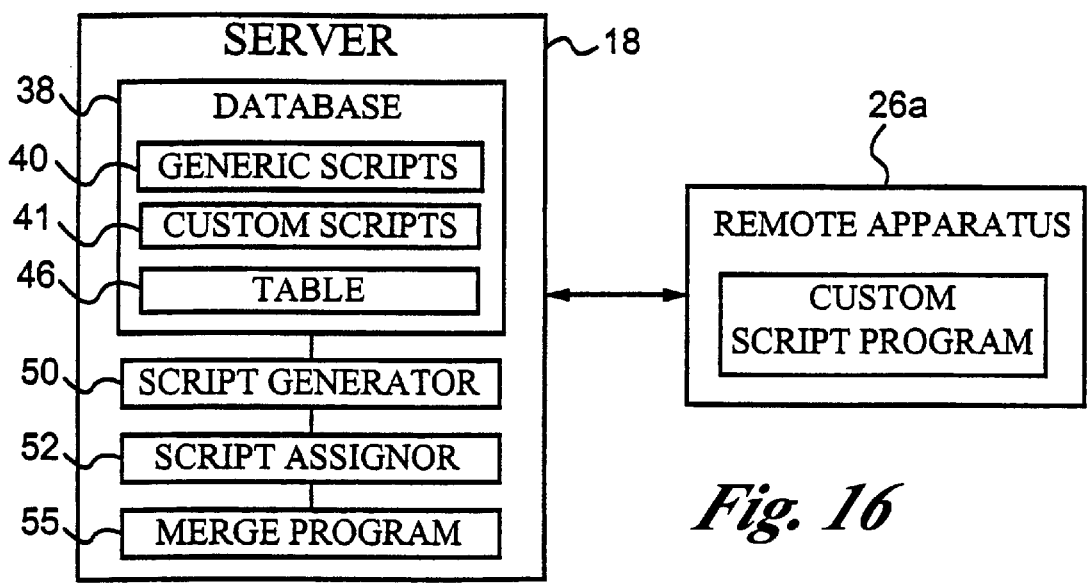
FIG. 16 is a schematic block diagram illustrating the interaction of the server of FIG. 1 with the apparatus of FIG. 3 according to a third embodiment of the invention.

The third embodiment also shows how the queries and statements may be customized to each individual by merging personal data with the script programs, much like a standard mail merge application. Referring to FIG. 16, personal data relating to each individual is preferably stored in look-up table 46 of database 38. By way of example, the data may include each individual's name, the name of each individual's physician, test results, appointment dates, or any other desired data. As in the preferred embodiment, database 38 also stores generic script programs 40 created by script generator 50.

Figure 17:
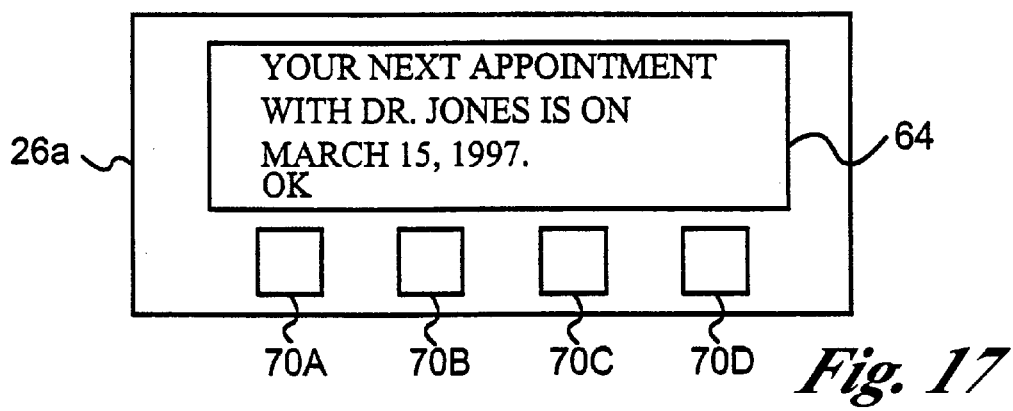
FIG. 17 is a first sample message appearing on the display of the apparatus of FIG. 3.
Figure 18:
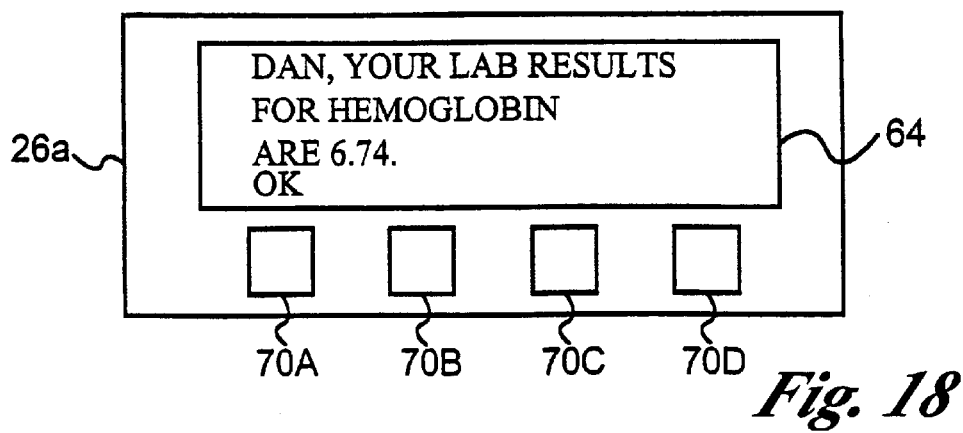
FIG. 18 is a second sample message appearing on the display of the apparatus of FIG. 3.

Server 18 includes a data merge program 55 for merging the data stored in table 46 with generic script programs 40. Data merge program 55 is designed to retrieve selected data from table 46 and to insert the data into statements in generic script programs 40, thus creating custom script programs 41. Each custom script program 41 contains statements which are customized to an individual. For example, the statements may be customized with the individual's name, test results, etc. Examples of such customized statements are shown in FIGS. 17–18.

Figure 19:
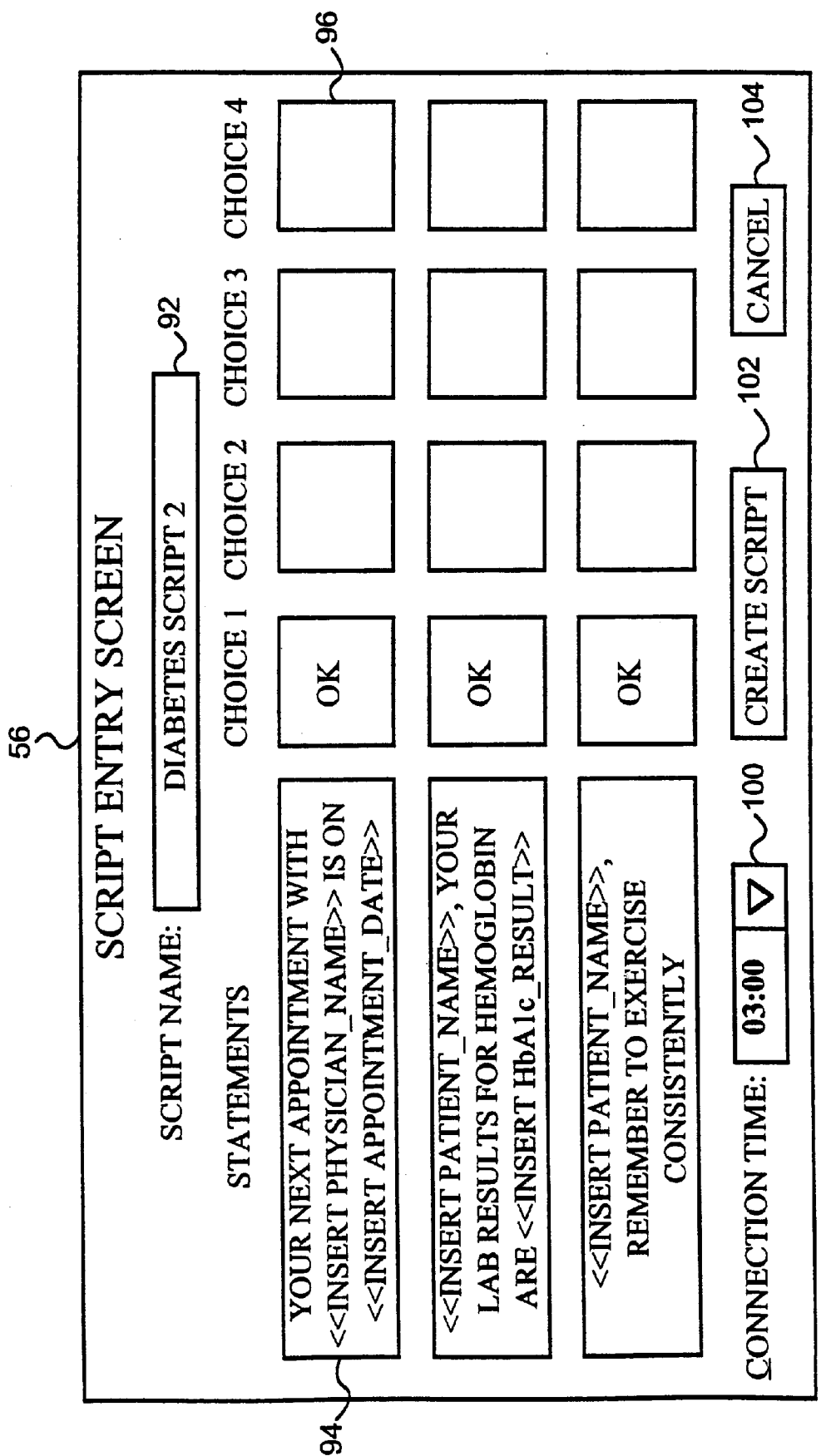
FIG. 19 is a script entry screen according to the third embodiment of the invention.

The operation of the third embodiment is similar to the operation of the preferred embodiment except that the script programs are used to communicate messages to the individuals rather than to query the individuals. Each message is preferably a set of statements. Referring to FIG. 19, the statements may be entered in server 18 through script entry screen 56, just like the queries of the preferred embodiment.

Each statement preferably includes one or more insert commands specifying data from table 46 to be inserted into the statement. The insert commands instruct data merge program 55 to retrieve the specified data from database 38 and to insert the data into the statement. For example, the insert commands shown in FIG. 19 instruct the data merge program to insert a physician name, an appointment date, a patient name, and a test result into the statements. As in the preferred embodiment, each statement may also include one or more response choices which are entered in fields 96.

Following entry of the statements and response choices, CREATE SCRIPT button 102 is pressed. When button 102 is pressed, script generator 50 generates a generic script program from the information entered in screen 56. The generic script program is similar to the script program shown in FIGS. 6A–6B, except that the display commands specify statements to be displayed rather than queries. Further, the statements include insert commands specifying data to be inserted into the script program. As in the preferred embodiment, multiple script programs are preferably generated, e.g. a generic script program for diabetes patients, a generic script program for asthma patients, etc. The generic script programs are stored in database 38.

Following generation of the generic script programs, server 18 receives script assignment information entered through script assignment screen 57. As shown in FIG. 7, the script programs are assigned by first selecting one of the generic script programs through check boxes 106, selecting individuals through check boxes 108, and pressing the ASSIGN SCRIPT button 112. When button 112 is pressed, data merge program 55 creates a custom script program for each individual selected in check boxes 108.

Each custom script program is preferably created by using the selected generic script program as a template. For each individual selected, data merge program 55 retrieves from database 38 the data specified in the insert commands. Next, data merge program 55 inserts the data into the appropriate statements in the generic script program to create a custom script program for the individual. Each custom script program is stored in database 38.

As each custom script program is generated for an individual, script assignor 52 assigns the script program to the individual. This is preferably accomplished by creating a pointer to the custom script program and storing the pointer with the individual's unique identification code in table 46. When the individual's remote apparatus 26*a–x* connects to server 18, server 18 receives from apparatus 26*a–x* the individual's unique identification code. Server 18 uses the unique identification code to retrieve from table 46 the pointer to the custom script program assigned to the individual. Next, server 18 retrieves the assigned script program from database 38 and transmits the script program to the individual's remotely programmable apparatus 26*a–x* through communication network 24.

Remotely programmable apparatus 26*a–x* receives and executes the script program. The execution of the script program is similar to the execution described in the preferred embodiment, except that statements are displayed to the individual rather than queries. FIGS. 17–18 illustrate two sample statements as they appear on display 64. Each statement includes a response choice, preferably an acknowledgment such as "OK". After reading a statement, the individual presses the button corresponding to the response choice to proceed to the next statement. Alternatively, the script program may specify a period of time that each statement is to be displayed before proceeding to the next statement. The remaining operation of the third embodiment is analogous to the operation of the preferred embodiment described above.

Figure 20A:
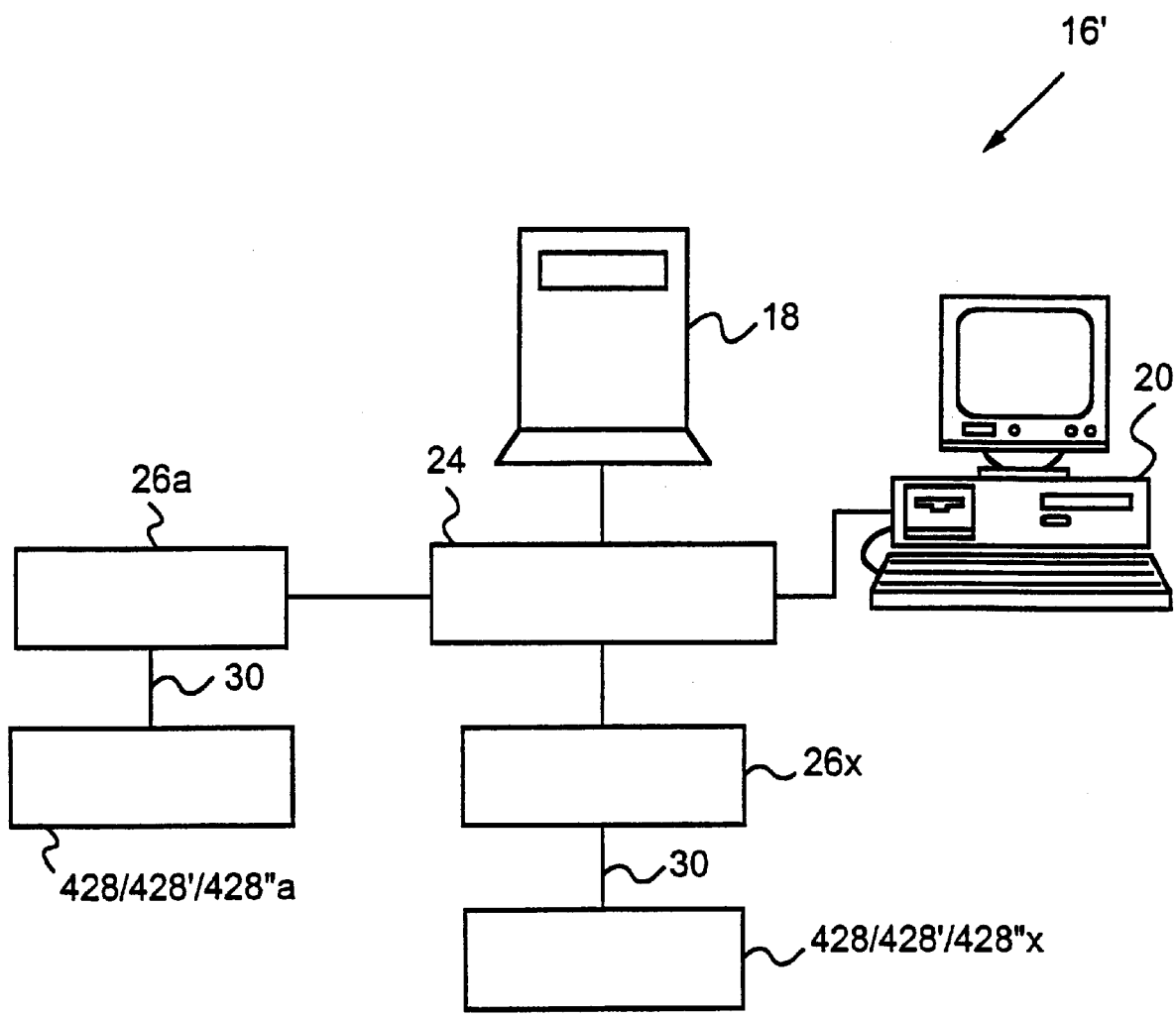
FIG. 20A is a block diagram of a networked monitoring system including a remote patient monitoring and drug dose measurement apparatus, according to another embodiment of the invention.

Although it is presently preferred to generate a custom script program for each individual as soon as script assignment information is received for the individual, it is also possible to wait until the individual's apparatus connects to server 18 before generating the custom script program. This is accomplished by creating and storing a pointer to the generic script program assigned to the individual, as previously described in the preferred embodiment. When the individual's remotely programmable apparatus 26*a–x* connects to server 18, data merge program 55 creates a custom script program for the individual from the generic script program assigned to the individual. The custom script program is then sent to the individual's remotely programmable apparatus 26*a–x* for execution. FIG. 20A is a block diagram of a networked monitoring system 16', according to a currently preferred embodiment of the invention. System 16' includes server 18, workstation 20 connected to server 18 through a communication network 24, and at least one remotely programmable apparatus 26*a–x*, essentially as described hereinabove with reference to FIG. 1. Each programmable apparatus 26*a–x* is in communication with server 18 through communication network 24, preferably the Internet. Alternatively, each patient's programmable apparatus, e.g., 26*a*, may be placed in communication with server 18 via wireless communication networks, cellular networks, telephone networks, or any other network which allows each apparatus 26*a–x* to exchange data with server 18. It is to be understood that system 16' may include any number of programmable apparatuses 26*a–x* for monitoring any number of patients. For clarity, only two programmable apparatuses 26*a–x* are shown in FIG. 20A. Workstation 20 may take the form of a health care provider or clinician's computer 426 (FIG. 20B).

Each remotely programmable apparatus 26*a–x* and its accompanying patient monitoring and drug delivery measurement apparatus 428/428'/428"*a–x* is for monitoring a patient and for recording a patient's activity. In particular, measurement apparatus 428/428'/428" (FIGS. 20B, 25, 31A, respectively) is adapted to provide measurements of a physiological condition of the patient, to produce measurements of a patient's treatment, to record the measurements, and to transmit the measurements to the patient's programmable apparatus 26*a–x*, e.g., through a standard connection cable 30. Each programmable apparatus 26*a–x* is in communication with server 18 through communication network 24, as described hereinabove, for transmitting measurement data from measurement apparatus, e.g., 428*a–x*, to workstation 20. Examples of suitable monitoring devices include blood glucose meters, respiratory flow meters, blood pressure cuffs, electronic weight scales, and pulse rate monitors. Examples of measurements of a patient's treatment include measurements of drug dose administered or self-administered to the patient. According to a currently preferred embodiment, such measurements include dose(s) of a drug administered to the patient via a syringe.

Figure 20B:
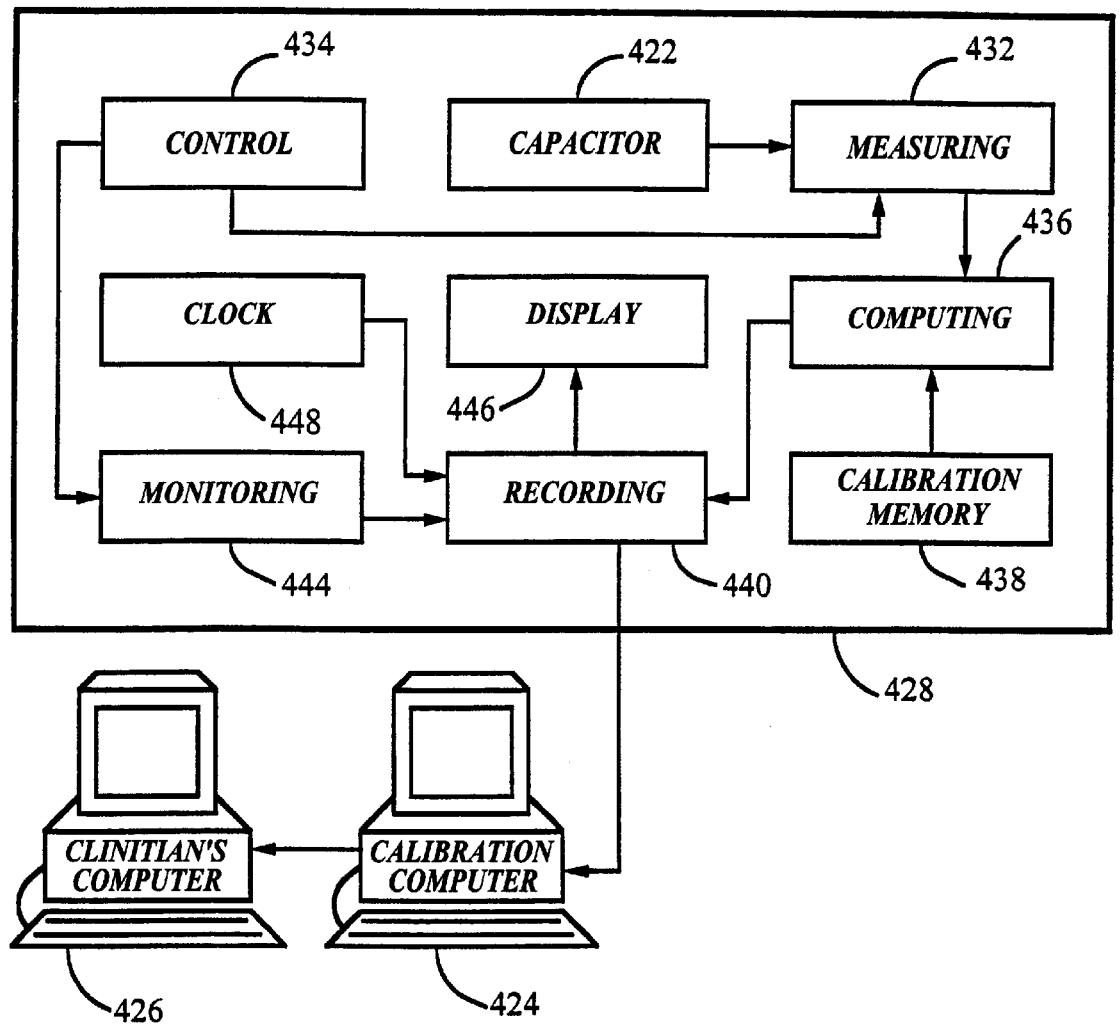
FIG. 20B is a high-level schematic diagram illustrating a patient monitoring and drug delivery measurement apparatus of the system of FIG. 20A, according to the invention.

FIG. 20B is a high-level schematic diagram illustrating a dose administration or drug delivery measurement apparatus 428 according to the invention. Apparatus 428 records data indicative of a dose of a drug or medication delivered to a patient from a syringe (e.g., syringe 580, FIG. 21). Apparatus 428 is capable of downloading the recorded data to a remotely programmable apparatus 26a–x (FIG. 20A).

According to one embodiment of the invention, remote apparatus 26a–x may take the form of a patient's computer 424, which in turn is capable of communicating with a clinician's computer 426 over a long-distance communication line such as a telephone line or the Internet, as shown in FIG. 20B. However, it is to be understood that apparatus 428 may be connected to other types of remote apparatus 26a–x, and thence via a communications network to a remote interface, as described hereinabove with reference to FIGS. 1–19 and elsewhere herein.

Figure 21:
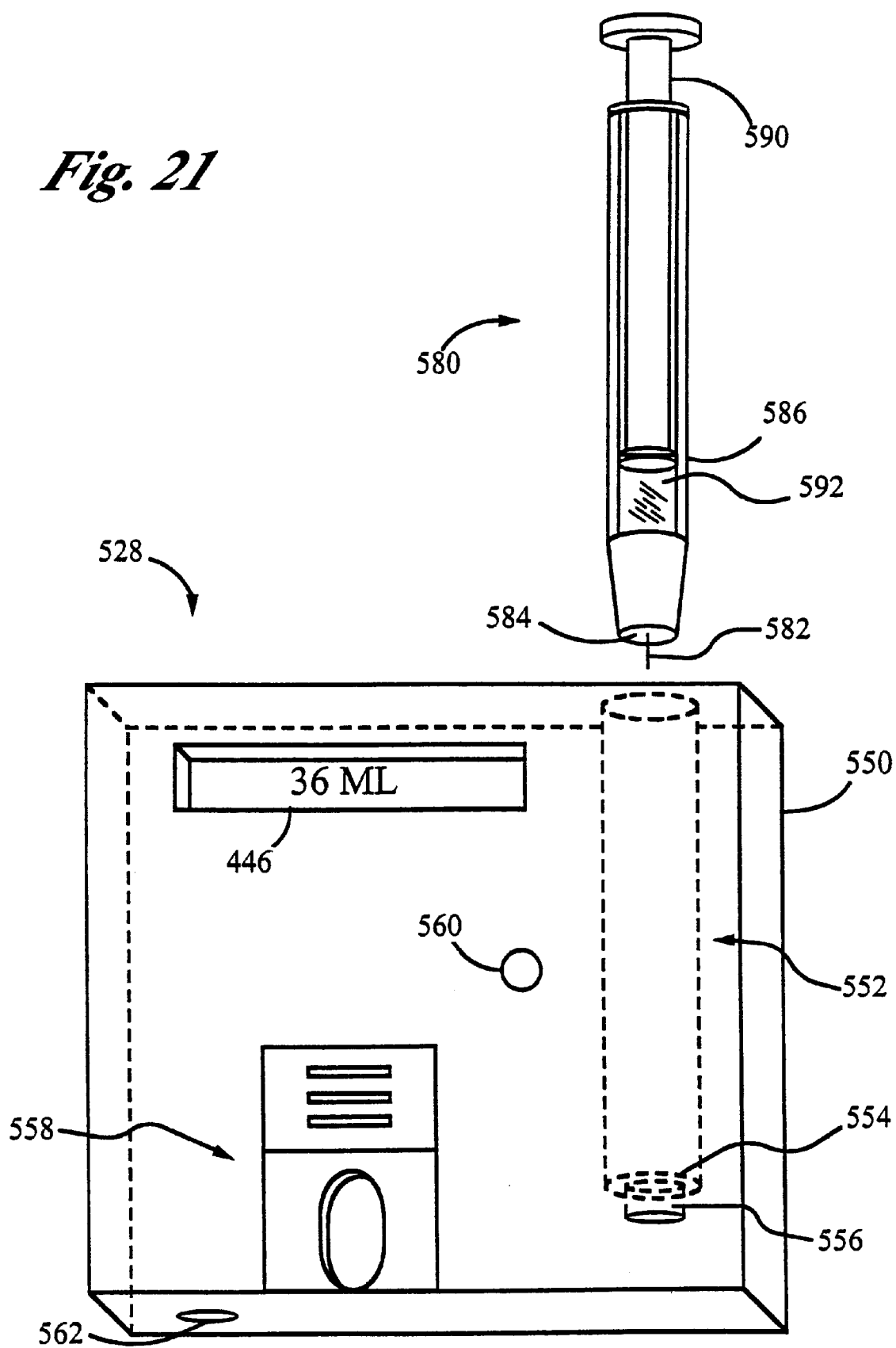
FIG. 21 is a perspective view of a drug delivery measurement apparatus according to another embodiment of the invention.
Figure 25:
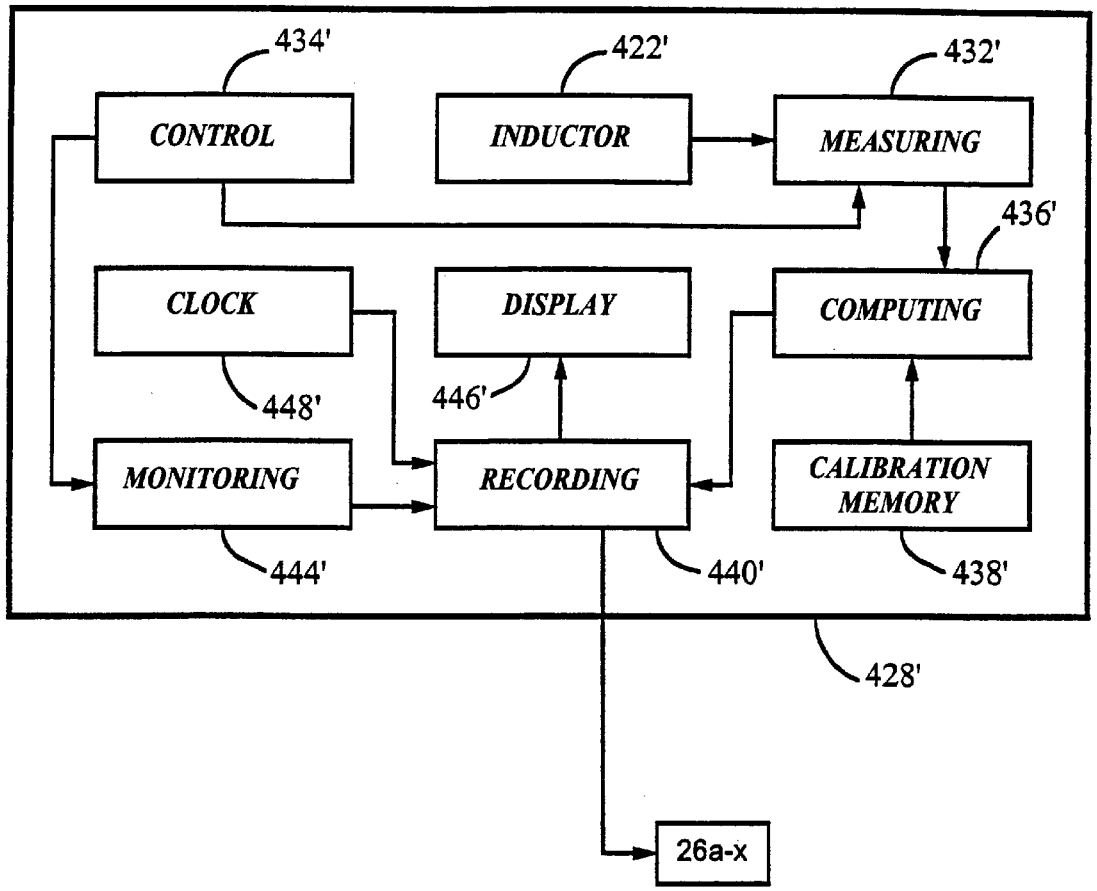
FIG. 25 is a high-level schematic diagram illustrating a patient monitoring and drug delivery measurement apparatus according to another embodiment of the invention.

Apparatus 428 includes a dose measurement element, in the form of a capacitive element 422 enclosing at least part of a syringe (e.g., syringe 580, FIG. 21). According to other embodiments of the invention, a dose measurement element may take other, distinct forms. For example, a dose measurement element may be in the form of an inductive element (FIGS. 25, 29A, 29B). Capacitive element 422 includes one or more capacitors arranged in a predetermined spatial relationship. A measuring device 432 is in electrical communication with capacitive element 422, and detects a capacitive response of capacitive element 422 when the syringe is in a predetermined measurement position. Measuring device 432 preferably includes a LC circuit with a resonant frequency $\omega=1/\sqrt{LC}$. Capacitance-measuring devices are well known in the art. The capacitive response of capacitive element 422 is indicative of the quantity of liquid in the syringe, and consequently of the dose administered to the patient using the syringe. A control device 434 is in electrical communication with measuring device 432, and temporally controls the operation of measuring device 432. Control device 434 is capable of turning-on measuring device 432 when a syringe is in the measurement position, for example before the administration of the dose to the patient.

Control device 434 preferably includes a button which the patient can press to trigger a measurement.

A computing device 436 is in electrical communication with measuring device 432 and with a calibration memory 438. Computing device 436 preferably includes a microprocessor. Computing device 436 is further in electrical communication with a recording device 440. Recording device 440 preferably includes a memory chip. Computing device 436 generates dose data to be stored in recording device 440. The dose data preferably includes a dose (e.g. an insulin dose) administered to the patient, but may be in general any data which can be used to reconstruct (for example, within system 428, at patient computer 24, or at clinician computer 426) the dose administered to the patient. In particular, computing device 436 calculates the quantity of liquid 592 within the syringe before injection of a dose, or the difference between the liquid quantities within the syringe before and after injection. Computing device 436 then sends the result (the dose) to recording device 440 for storage.

According to the embodiment of FIG. 20B, computing device 436 determines liquid quantities by comparing capacitive response data received from measuring device 432 with predetermined calibration data stored in calibration memory 438. The calibration data is indicative of the correspondence between capacitive responses and liquid quantities for the entire range of potential liquid quantities in the syringe. That is, calibration memory 438 stores the quantity of liquid 592 corresponding to a given capacitive response of capacitive element 422, for all liquid quantities potentially present in the syringe.

A monitoring device 444 is electrically connected to recording device 440. Monitoring device 444 tests a physical or physiological condition of the patient, and generates condition data representative of the physical or physiological condition. Preferably, the condition is diabetes, the monitoring device includes a blood glucose meter, and the condition data includes a blood glucose level of the patient. Recording device 440 records the condition data generated by monitoring device 444. A display 546 is electrically connected to recording device 440, and displays dose data and condition data to the patient. Display 446 can be a liquid crystal display (LCD). A display such as display 446 may be directly connected to computing device 436 and monitoring device 444, rather than indirectly through recording device 440. A digital clock 448 is connected to recording device 440. Upon prompting, clock 448 sends the current date and time to recording device 440 for recording in conjunction with dose and/or condition data.

FIG. 21 shows a perspective view of a measurement apparatus 528, according to a preferred embodiment of the present invention. Apparatus 528 includes a housing 550 enclosing the various electronic components of apparatus 528. Housing 550 preferably includes a metal layer for shielding internal components of apparatus 528 from external electric fields, and in particular the capacitive components of apparatus 528 (see below). As is apparent to the skilled artisan, care should also be taken to minimize all stray capacitances. Housing 550 is sufficiently compact to allow apparatus 528 to be hand-held and carried by a user.

Display 446 is preferably recessed within housing 550. A patient interface 558 (of monitoring device 444, FIG. 20B) is also coupled to housing 550. In a preferred embodiment, the patient places a finger on patient interface 558, allowing monitoring device 444 to perform a blood glucose measurement for the patient. Blood glucose meters are well known in the art and will not be discussed here in detail. A dose measurement control 560 (of control means 434, FIG. 20B) is coupled to housing 550, and allows the patient to specify when dose measurements are to be performed by apparatus 528 (see below). A port 562 allows data transfer between recording device 440 and patient computer 424 (FIG. 20B).

Housing 550 also encloses a holder 552 for receiving and snugly holding a syringe 580 in the measurement position. A circular opening 553 within housing 550 provides access to holder 552. Holder 552 has a well-like shape for laterally enclosing syringe 580. Holder 552 defines an enclosed space 556 opposite opening 553, for accommodating a needle 582 of syringe 580 when syringe 580 is in the measurement position. Syringe 580 can be a conventional syringe, such as a plastic syringe. Syringe 580 includes a barrel 586 and a plunger 590, defining a space for a liquid 592. Liquid 592 preferably includes insulin. Plunger 590 is capable of longitudinal motion relative to barrel 586, for adjusting the volume available to liquid 592. Holder 552 includes an alignment ledge 554 for aligning barrel 586 to holder 552 in the measurement position. A contact surface 584 of syringe 580 is in contact with alignment ledge 554 when syringe 580 is in the measurement position.

Figure 22A:
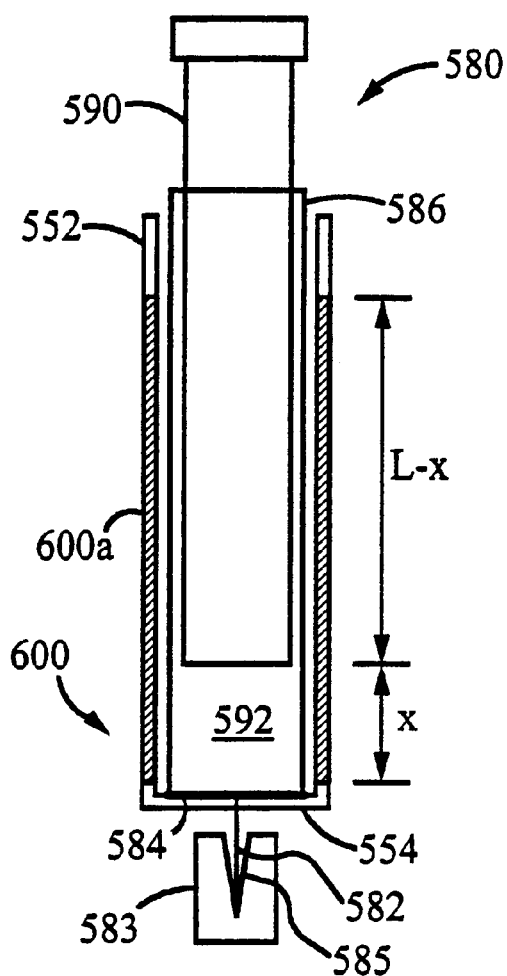
FIG. 22A is a longitudinal sectional view of a syringe situated in a measurement position within a holder of the apparatus of FIG. 21, according to one embodiment of the invention.
Figure 22B:
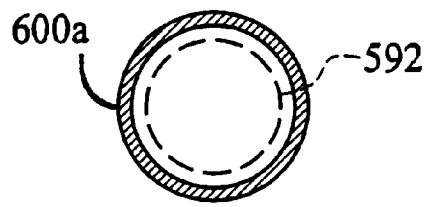
FIG. 22B is a transverse sectional view of the holder and syringe of FIG. 22A.

FIG. 22A shows a longitudinal sectional view through syringe 580 and holder 552, with syringe 580 in the measurement position. FIG. 22B shows a transverse sectional view of the arrangement of FIG. 22A. A capacitive element 600 consists of a single capacitor defined between an electrode 600a and liquid 592. Electrode 600a is a cylindrical copper sheet embedded in a plastic side wall of holder 552, and is electrically connected to measuring device 432 (FIG. 20B). Electrode 600a encloses syringe 580 externally and laterally. Liquid 592 is connected to measuring device 432 through needle 582 and a needle contact 583 coupled to holder 552. Needle contact 583 is a corrosion-resistant metal block having a sloped (conical) side wall 585 for contacting needle 582 when syringe 580 is in the measurement position.

The dielectric constant within capacitive element 600 is relatively spatially invariant and does not change substantially with the quantity of liquid 592. The dielectric constant within capacitive element 600 is determined by the materials and/or thicknesses of barrel 586, the air between barrel 586 and the side wall of holder 552, and the portion of the side wall of holder 552 between electrode 600a and barrel 586. Neglecting edge effects and effects stemming from the non-ideal conductivity of liquid 592, the capacitance of capacitive element 600 is then primarily determined by its surface area, which is proportional to the longitudinal extent x of liquid enclosed by electrode 600a.

To operate measurement apparatus 528, a patient inserts the manufacturer-provided syringe 580 in holder 552 prior to administration of the dose. When syringe 580 is pressed against alignment ledge 554 and needle 582 contacts needle contact 583, syringe 580 is in the measurement position. The patient presses dose measurement control (e.g., button) 560 (FIG. 21) to activate measuring device 432. Measuring device 432 performs a measurement of the capacitance of capacitive element 600. Computing device 436 then determines the quantity of liquid 592 within syringe 580. Recording device 440 records the liquid quantity as the administered dose, in conjunction with the current date and time obtained from clock 448. Recording device 440 may also record condition data received from monitoring device 444, and the associated date and time. Recording device 440 then contains the patient's blood glucose and insulin dose histories. The patient periodically (e.g. weekly) connects his or her measurement apparatus 528 to patient computer 424 and downloads the histories stored in recording device 440. The histories may then be periodically transmitted to clinician's computer 426.

Figure 23A:
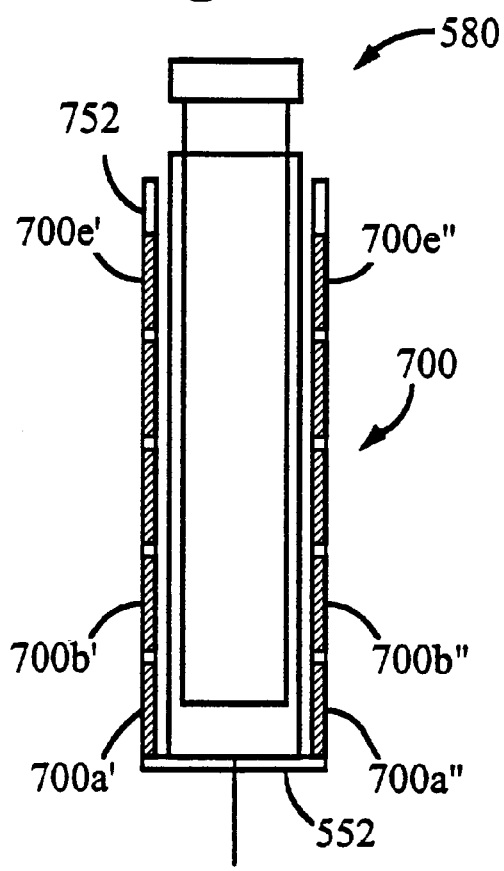
FIG. 23A is a longitudinal sectional view of a syringe, holder, and capacitor arrangement, according to another embodiment of the invention.
Figure 23B:
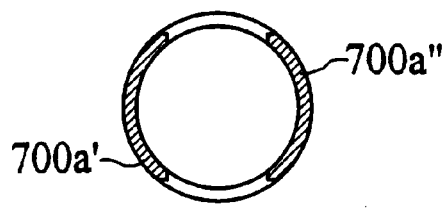
FIG. 23B is a transverse sectional view of the holder and syringe of FIG. 23A.

FIG. 23A shows a longitudinal sectional view of an alternative capacitive element geometry of the present invention, while FIG. 23B shows a transverse sectional view of the geometry of FIG. 23A. A capacitive element 700 is coupled to holder 552, and is situated completely externally to syringe 580. Capacitive element 700 includes a plurality of independent, longitudinally spaced, stacked capacitors 700a–e. Each capacitor 700a–e is independently connected to measuring device 432 (FIG. 20B), and measuring device 432 determines the capacitive response of each capacitor 700a–e independently. A capacitive response pattern of capacitive element 700 (the ensemble of capacitive responses of capacitors 700a–e) is indicative of the quantity of liquid 592 within syringe 580. The use of plural stacked capacitors reduces the vulnerability of a system of the present invention to dosage determination errors caused by a constant capacitance offset.

Capacitor 700a includes electrodes 700a', 700a" embedded within the side wall of holder 552 on opposite sides of syringe 580. Capacitors 700b–e are similar to capacitor 700a and are stacked above capacitor 700a. The surface area of each capacitor 700a–e is constant, and does not depend on the quantity of liquid 592. The effective dielectric constant of each capacitor 700a–e may depend, however, on the quantity of liquid 592. If liquid 592 is substantially conductive, it behaves like an electrode inserted between electrodes 700a', and 700a", thus creating two capacitors in series: one defined by electrode 700a' and liquid 592, the other defined by liquid 592 and electrode 700a". Preferably, the dielectric properties of barrel 586, plunger 590 and liquid 592 are such that the capacitance response pattern of capacitive element 700 is indicative of the position of plunger 590 relative to capacitive element 700 and/or of the quantity of liquid 592 within syringe 580.

Figure 24A:
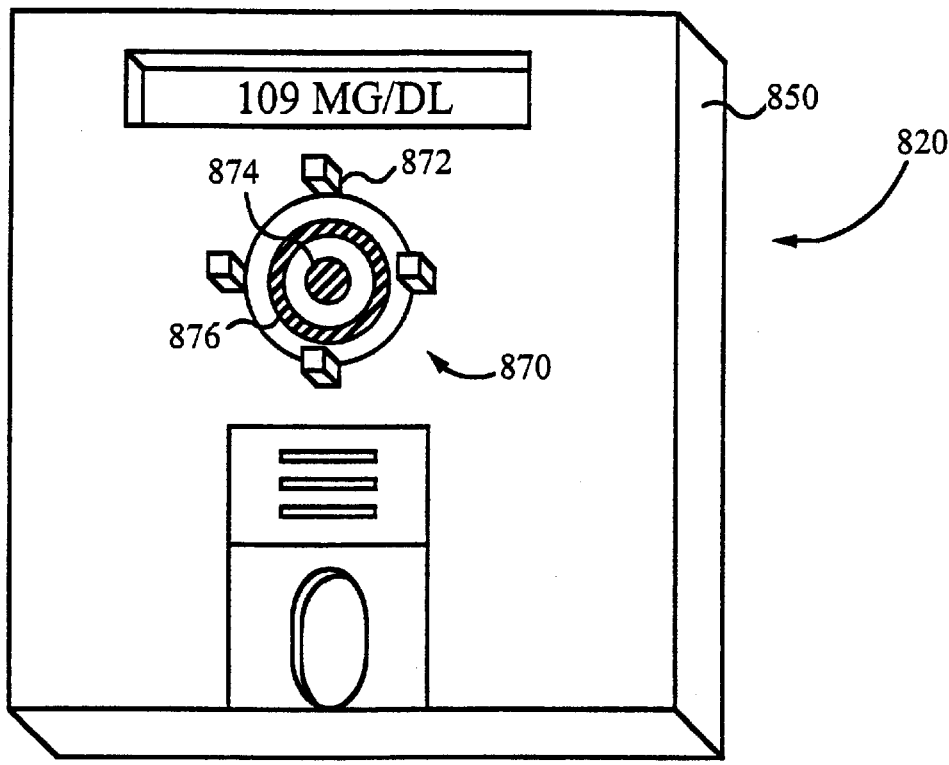
FIG. 24A is a perspective view of an apparatus suitable for use with a syringe, the apparatus comprising an internal capacitor, according to one embodiment of the invention.

FIG. 24A shows a perspective view of an alternative apparatus 820 of the present invention, suitable for measuring doses delivered by syringes using either capacitors or inductors for dose measurement (FIGS. 22A–23B and 27A–28, respectively). A circular placement field 870 is delineated on the outside of a housing 850 of apparatus 820. Placement field 870 is bordered on four sides by a set of rigid positioning studs 872 forming a holder. Placement field 870 includes a circular input contact 874 positioned at the center of field 870, and a ring-shaped output contact 876 positioned concentrically to input contact 874. Input contact 874 and output contact 876 are made of an electrically conductive material, preferably copper, and are connected to measuring device 432 (FIG. 20B) or measuring device 432' (FIG. 25).

Figure 24B:
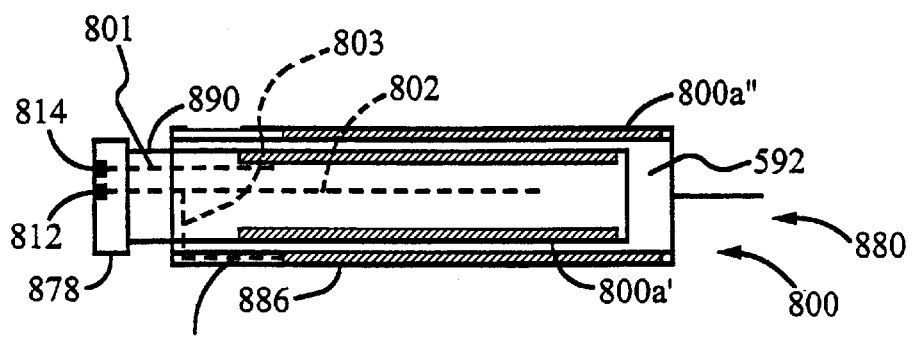
FIG. 24B is a longitudinal sectional view of a syringe capacitor geometry suitable for use with the apparatus of FIG. 24A.

FIG. 24B shows a longitudinal sectional view of a syringe 880 suitable for use with the apparatus of FIG. 24A. Syringe 880 includes a plunger 890 positioned within a barrel 886. Plunger 890 includes a cylindrical cap 878 sized so as to fit on placement field 870 between studs 872 when syringe 880 is in a measurement position. Cap 878 includes an input terminal 812 and an output terminal 814 situated such that input terminal 812 and output terminal 814 are in electrical communication respectively with input contact 874 and output contact 876 when syringe 880 is in the measurement position.

A metallic contact line 801 within plunger 890 establishes electrical communication between output terminal 814 and a cylindrical electrode 800a' situated embedded within the plastic body of plunger 890, along the outside surface of lunger 890. A second cylindrical electrode 800a" is encapsulated in the plastic body of barrel 886, and is co-axial with electrode 800a'. Electrode 800a" is in electrical communication with input terminal 812 through metallic contact lines 802 and 804. Line 802 is situated on the lateral (outside) surface of plunger 890, while line 804 is situated within barrel 886. A sliding electrical contact schematically illustrated as 803 is established between a fixed exposed point of line 804 and various points of line 802 as plunger 890 is moved within barrel 886.

The following discussion is intended to illustrate a measurement apparatus of the invention which utilizes a capacitive element, and should not be construed to limit the invention. Consider the geometry of FIGS. 22A and 22B, for a typical syringe. Neglecting edge effects, the capacitance of capacitive element 600 is approximately $$C \approx 2\pi\varepsilon_{bar} x \ln\left(\frac{b}{a}\right) \quad [1]$$

where x is the length of capacitor 600, a and b are the radii of the cylinders defined respectively by liquid 592 and electrode 600a, and ϵbar is the effective dielectric constant between liquid 592 and electrode 600a. From eq. [1] it can be seen that dC/dx, the variation of the capacitance of capacitor 600 with displacement x, can be maximized for given radii a and b by increasing ϵbar Thus, materials with high dielectric constants are preferred for the space between liquid 592 and electrode 600a.

FIG. 25 is a high-level schematic diagram illustrating a dose administration or drug delivery measurement apparatus 428' according to another embodiment of the instant invention. As for apparatus 428 described hereinabove with reference to FIG. 20B, apparatus 428 records data indicative of dose(s) delivered to a patient from a syringe (e.g., syringe 580'). Apparatus 428' is capable of downloading the recorded data to a remotely programmable apparatus (e.g., apparatus 26a–26x, (FIGS. 1, 20A). According to the invention, a remotely programmable apparatus 26a–26x may take the form of a patient computer 424 (FIG. 20B), which in turn is capable of communicating with a clinician's computer 426 (FIG. 20B) over a communication network or long-distance communication line, essentially as described hereinabove with reference to FIGS. 1–20B.

Apparatus 428' includes an inductive element 423 enclosing at least part of the syringe. Inductive element 423 includes one or more inductors arranged in a predetermined spatial relationship. A measuring device 432' is in electrical communication with inductive element 423, and detects an inductive response of inductive element 423 when the syringe is in a predetermined measurement position. Measuring device 432' preferably includes a LC circuit with a resonant frequency ($\omega=1/\sqrt{LC}$. Inductance-measuring devices are well known in the art. The inductive response of inductive element 423 is indicative of the quantity of liquid in the syringe, and consequently of the dose administered to the patient using the syringe. Apparatus 428' further includes a control device 434' in electrical communication with a measuring device 432'; a computing device 436' in electrical communication with measuring device 432' and with a calibration memory 438'; and a recording device 440', somewhat analogous to apparatus 428, described hereinabove with reference to FIG. 20B. Computing device 436' is further in electrical communication with a recording device 440'.

Computing device 436' preferably includes a microprocessor. Recording device 440' preferably includes a memory chip. Computing device 436' generates dose data to be stored in recording device 440'. The dose data preferably includes a dose (e.g. an insulin dose) administered to the patient, essentially as described hereinabove with reference to apparatus 428. Computing device 436' sends the result (the dose) to recording device 440' for storage.

Computing device 436' determines liquid quantities by comparing inductive response data received from measuring device 432' with predetermined calibration data stored in calibration memory 438'. The calibration data is indicative of the correspondence between inductive responses and liquid quantities for the entire range of potential liquid quantities in the syringe. That is, calibration memory 438' stores the liquid quantity corresponding to a given inductive response of inductive element 423, for all liquid quantities potentially present in the syringe.

Apparatus 428' further includes a monitoring device 444' electrically connected to recording device 440', a display 446' also electrically connected to recording device 440', and a digital clock 448' connected to recording device 440', analogous to the corresponding components of apparatus 428 described hereinabove with reference to FIG. 20B. Upon prompting, clock 448' sends the current date and time to recording device 440' for recording in conjunction with dose or condition data related to the patient being monitored.

Figure 26:
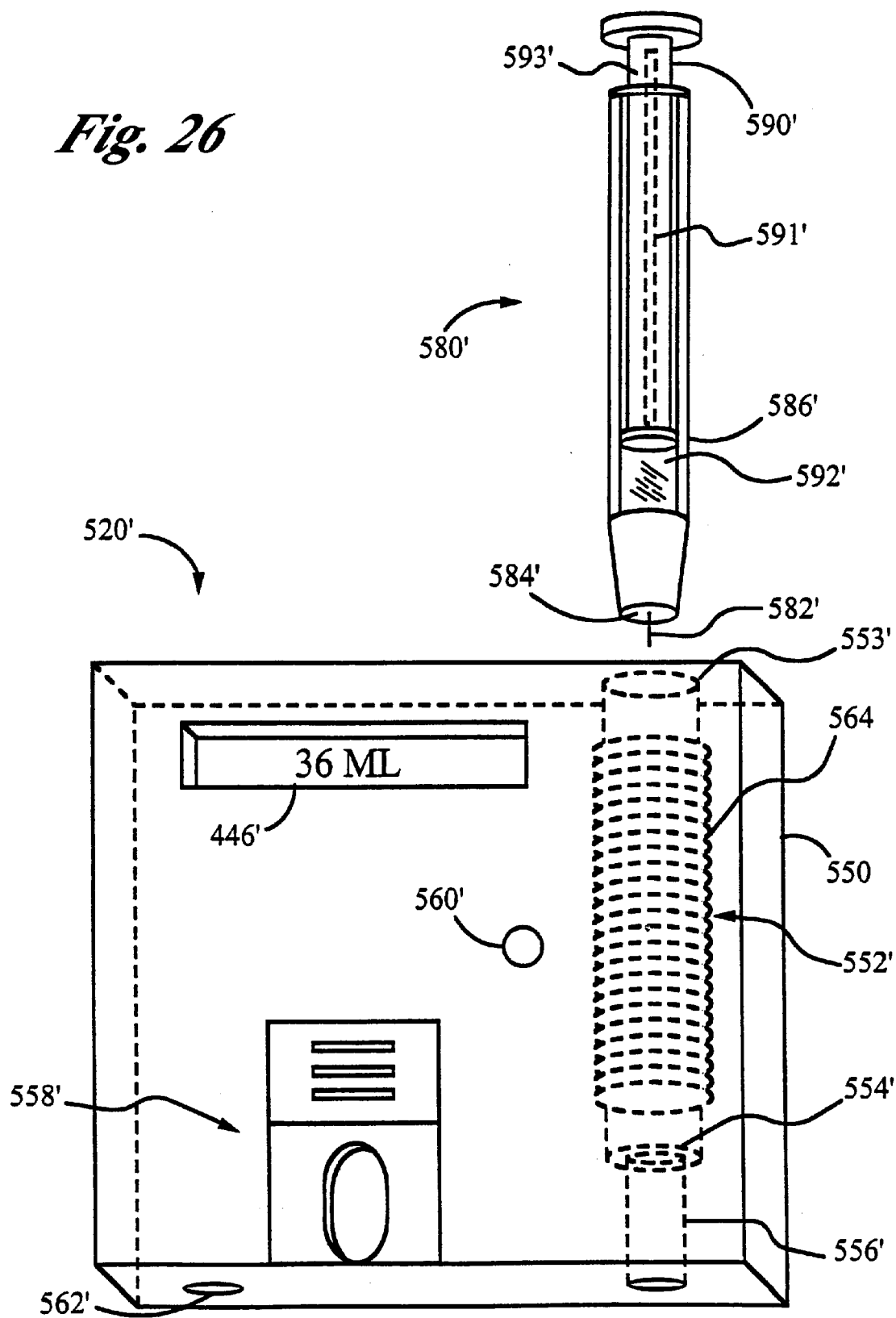
FIG. 26 is a perspective view of a drug delivery measurement apparatus according to another embodiment of the invention.

FIG. 26 shows, in perspective view, an apparatus 528', according to one embodiment of the present invention. Apparatus 528' includes a housing 550' enclosing the various electronic components of apparatus 528'. Housing 550' preferably includes a metal layer for magnetically shielding internal components of apparatus 528', in particular inductive components of apparatus 528' (see below). Housing 550' is compact and has dimensions and weight characteristics similar to those described hereinabove with respect to housing 550 of FIG. 21. Housing 550' includes a (recessed) display 446' and a patient interface 558' (of monitoring device 444', FIG. 25) coupled to housing 550', similar to housing 550 of FIG. 21.

In a preferred embodiment, the patient places a finger on patient interface 558', allowing monitoring device 444' to perform a blood glucose measurement for the patient. A dose measurement control 560' (of control device 434', FIG. 25) is coupled to housing 550', and allows the patient to specify when dose measurements are to be performed by apparatus 528' (see below). A port 562' allows data transfer between recording device 440' and a patient computer or remotely programmable apparatus (not shown).

Housing 550' also encloses a holder 552' for receiving and holding a syringe 580' in the measurement position.

Syringe 580' corresponds specifically to the calibration data stored in calibration memory 438'. A circular opening 553' within housing 550' provides access to holder 552'. Holder 552' has a well-like shape for laterally enclosing syringe 580'. Holder 552' defines an enclosed space 556' opposite opening 553', for accommodating a needle 582' of syringe 580' when syringe 580' is in the measurement position. Enclosed space 556' is preferably closed off, so as to prevent accidental access to needle 582' while syringe 580' is in the measurement position.

Syringe 580' includes a barrel 586' and a plunger 590', defining a space for a liquid 592. Plunger 590' preferably includes a longitudinal strip 591' made of a ferromagnetic material such as ferrite, embedded in a plastic body 593'. Alternatively, a standard syringe with a plunger consisting of a plastic body can be used with a device of the present invention. Plunger 590' is capable of longitudinal motion relative to barrel 586', for adjusting the volume available to liquid 592. Holding device 552' includes an alignment ledge 554' for aligning barrel 586' to holder 552' in the measurement position. A contact surface 584' of syringe 580' is in contact with alignment ledge 554' when syringe 580' is in the measurement position.

A cylindrical inductor 564 is mechanically coupled to holder 552', and encloses syringe 580' externally and laterally. Inductor 564 encloses syringe 580' along the entire longitudinal extent along which the position of plunger 590' and/or the quantity of liquid 592 may vary. The position of plunger 590' and/or the quantity of liquid 592 within syringe 580' determine the inductance of inductor 564. The magnetic permeabilities of plunger 590' and liquid 592 are substantially different, such that the inductance of inductor 564 is indicative of the position of plunger 590' relative to inductor 564 and of the quantity of liquid 592 within syringe 580'. In particular, the two permeabilities differ by at least a factor of two, preferably by a factor of ten or more.

The operation of apparatus 528' by a patient is similar to the operation of apparatus 528 as described hereinabove. Briefly, a patient inserts the manufacturer-provided syringe 580' in holder 552' prior to administration of the dose. When syringe 580' is pressed against alignment ledge 554', syringe 580' is in the measurement position. The patient presses dose measurement control (button) 560' to activate measuring device 432'. Measuring device 432' (FIG. 25) performs measurement of the inductance of inductor 564. Computing device 436' then determines the quantity of liquid 592 within syringe 580'. Recording device 440' records liquid quantity as the administered dose, in conjunction with current date and time from clock 448". Recording device 440' may also record condition data received from monitoring means 444', and the associated date and time. The patient periodically connects apparatus 528' to a remotely programmable apparatus 26a–x or to a patient computer (not shown) and downloads the patient's blood glucose and insulin dose histories stored in recording device 440' for periodic transmission to, e.g., a clinician's computer (also not shown).

FIG. 27A shows a longitudinal sectional view of a syringe 980, according to one embodiment of the invention, while FIG. 27B shows a transverse sectional view of syringe 980. Syringe 980 is suitable for use with the apparatus of FIG. 24A, and includes a plunger 990 positioned within a barrel 986. Plunger 990 includes a cylindrical ferromagnetic core 991 encapsulated within a plastic shell 993. Plunger 990 also includes a cylindrical cap 978 sized so as to fit on placement field 470 (FIG. 24A) between studs 472 when syringe 980 is in a measurement position. Cap 978 includes an input terminal 912 and an output terminal 914 situated such that input terminal 912 and output terminal 914 are in electrical communication respectively with input contact 474 and output contact 476 when syringe 980 is in the measurement position. Barrel 986 includes an inductor 900 encapsulated within a plastic side wall. Metallic contact lines 903, 905 (located within plunger 990 and barrel 986) establish electrical communication between inductor 900 and input terminal 912 and output terminal 914, respectively. For taking a measurement, the patient places syringe 980 on placement field 470 and activates measuring device 432' to measure the inductance of inductor 900.

FIG. 28 shows a longitudinal sectional view of an alternative geometry for an inductance-enhanced syringe 1080 of the present invention. A plunger 1090 of syringe 1080 includes an inductance-enhancing element 1091 having a plurality of longitudinally spaced distinct segments 1095, embedded in a plastic shell 1093. Segments 1095 are thin ferromagnetic disks stacked along the longitudinal direction of plunger 1090. Segments 1095 have a magnetic permeability substantially higher than that of plastic shell 1093 or liquid 592.

FIGS. 29A and 29B illustrate an alternative inductor geometry of the present invention. An inductive element 1100, coupled to and enclosing holder 552', is formed by a plurality of independent longitudinally-spaced, stacked inductors 1101a–c. Measuring device 432' is used to measure an inductive response pattern of inductors 1101a–c. The response pattern preferably consists of the inductance of each inductor 1101a–c. The longitudinal extent of each inductor 1101a–c is much greater than the desired resolution achievable with inductive element 1100. In the embodiment illustrated in FIG. 29B, the longitudinal extent of each inductor 1201a–p of an inductive element 1200 is of the same order of magnitude as the desired resolution to be achieved with inductive element 1200. The use of plural longitudinally stacked inductors 1201a–p reduces the vulnerability of a system of the present invention to dosage determination errors caused by a constant inductance offset.

Figure 30A:
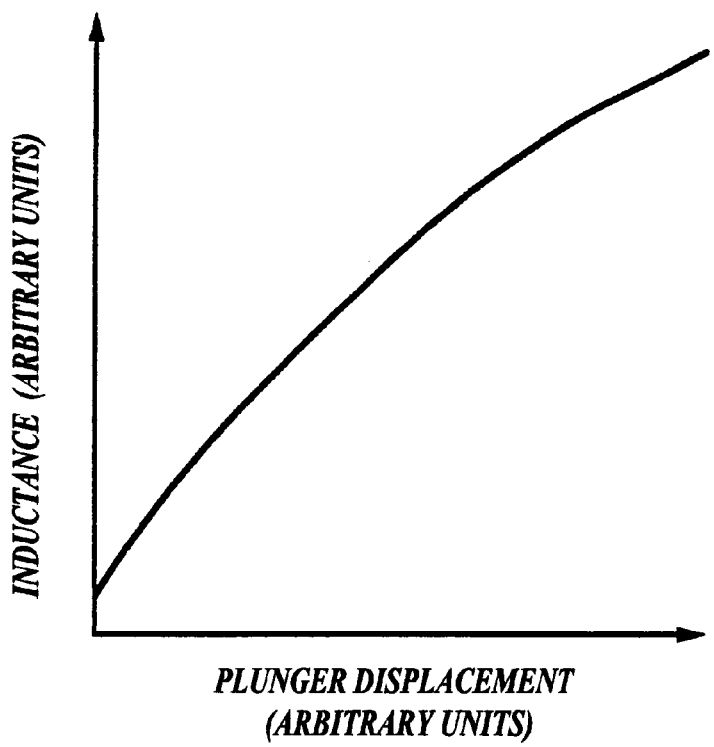
FIG. 30A illustrates qualitatively the dependence of inductance with plunger displacement for the geometry shown in FIG. 26.
Figure 30B:
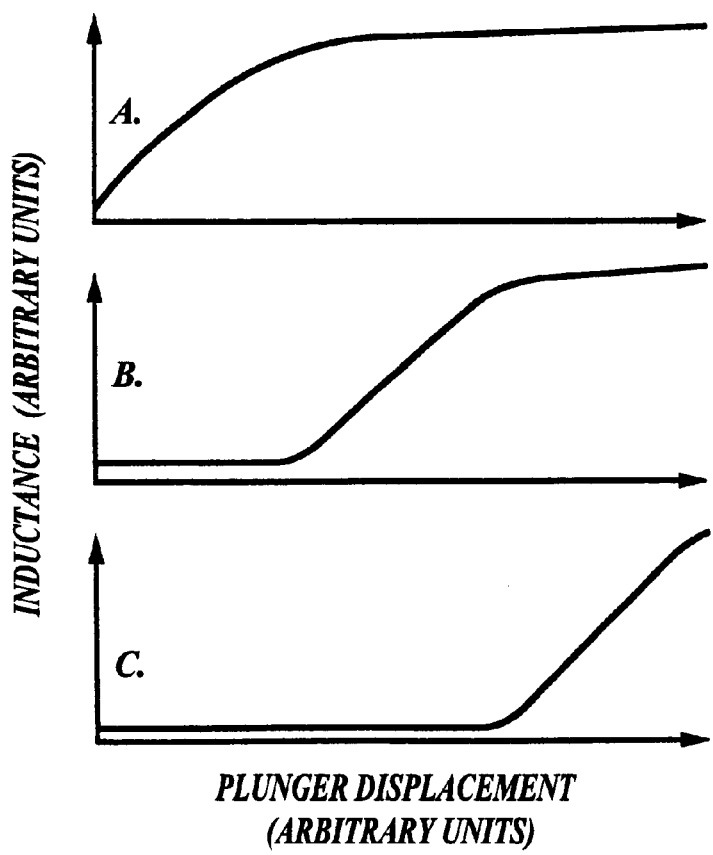
FIG. 30B illustrates qualitatively the dependence of inductance with plunger displacement for each inductor in the geometry of FIG. 29A.

FIGS. 30A and 30B illustrate qualitatively the variation of inductance with plunger displacement for the inductive element geometries of FIGS. 26 and 29A, respectively. In FIGS. 30A and 30B, the plunger is taken to have a higher effective magnetic susceptibility than the liquid in the syringe. The inductance of inductor 564 increases with the extent of plunger 590' enclosed by inductor 564, as illustrated in FIG. 30A. The plunger displacement and delivered dose are computed from the measured inductance and stored calibration data. Likewise, the response pattern of inductive element 1100 changes as more of plunger 590' becomes enclosed by inductive element 1100. For a small dose to be delivered (small plunger displacement), plunger 590' is enclosed only by inductor 1101a but not by inductors 1101b–c. For a large dose to be delivered (large plunger displacement, or plunger pushed in close to the syringe needle), plunger 590' is completely enclosed by inductors 1101a–b and only partially enclosed by inductor 1101c.

The following discussion is intended to illustrate a measurement apparatus of the invention which utilizes an inductive element, and should not be construed to limit the invention. Consider a geometry similar to those shown in FIGS. 26 or 27A, for a typical inductance-enhanced syringe. Consider a position of plunger 990 in which an inductor encloses a length x of liquid and a length D-x of plunger (see FIG. 27A). From the inductance of an ideal long solenoid of length D, cross-sectional area A, and turn density (number of turns per unit length) n, $$L = \mu n^2 DA, \quad [2]$$

one can obtain an order-of-magnitude estimate of the total inductance of the inductor as a function of x. Neglecting edge effects, $$L_{tot} \approx L_{liq} + L_{plg} \approx n^2 A(\mu_{liq}x + \mu_{plg}(D-x)) = \quad [3]$$
$$n^2 A(x(\mu_{liq} - \mu_{plg}) + \mu_{plg}D),$$

where $\mu_{liq}$ and $\mu_{plg}$ are magnetic permeabilities, and $L_{liq}$ and $L_{plg}$ are inductances corresponding respectively to the liquid and the plunger. As illustrated by eq. [3], the sensitivity of $L_{tot}$ to variations in x increases with the difference between the magnetic permeabilities of the plunger and the liquid.

For a ferromagnetic-core plunger and corresponding solenoid, n is on the order of $10^5$ m$^{-1}$, A is on the order of $10^{-5}$ m$^2$, and $\mu_{liq}$ and $\mu_{plg}$ are, respectively, on the order of $10\,\mu_o$ for water and $>10^3\,\mu_o$ for a typical ferromagnetic or ferrimagnetic material. The above values yield a sensitivity on the order of $10^2$ mH per mm of plunger displacement. The inductor sensitivity may be lower for a ferrite-strip plunger or for a conventional plastic plunger. The inductor sensitivity may also be lower for other inductor geometries. The corresponding sensitivity of the inductance-measuring device may be adjusted according to the particular inductor geometry and plunger used; generally a more sensitive measuring device will be needed for measuring displacements of plungers having an effective permeability closer to that of the liquid.

Figure 31A:
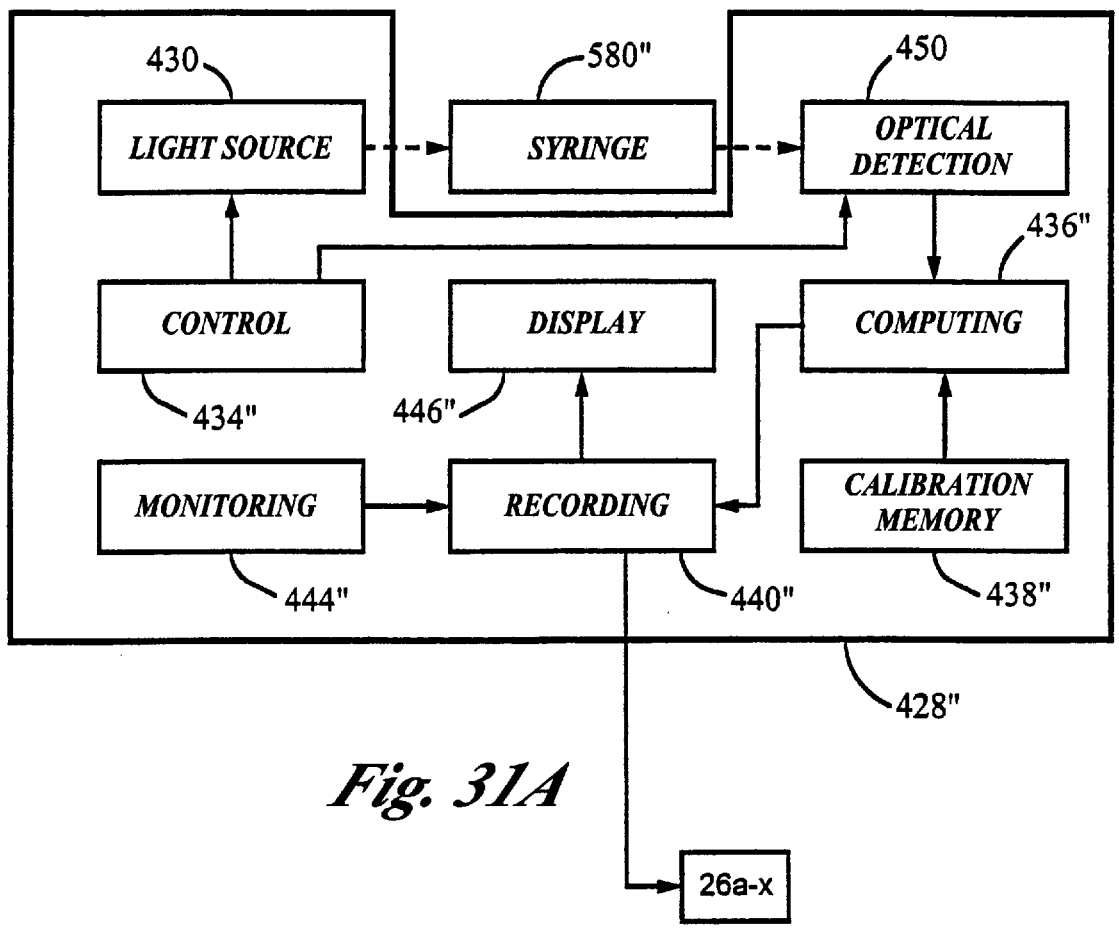
FIG. 31A is a high-level schematic diagram illustrating a patient monitoring and drug delivery measurement apparatus, according to another embodiment of the invention.

FIG. 31A is a high-level schematic diagram illustrating a measurement apparatus 428" according to another embodiment of the invention. Optical connections are indicated in FIG. 31A by dashed lines, while electrical connections are indicated by solid lines. Apparatus 428' records data indicative of doses delivered to a patient using a syringe 580". Apparatus 428" is capable of downloading the recorded data to a remotely programmable apparatus 26a–x (FIGS. 1, 20A), such as a patient computer 424 (FIG. 20B), which in turn is capable of communicating with workstation (FIGS. 1, 20A), or a clinician's computer 426 (FIG. 20B) over a communication network, telephone line, or the Internet.

Apparatus 428" includes a light source 430 and an optical detector 450 for optical communication with syringe 580" when the latter is in a measurement position. Light source 430 generates light incident on syringe 580". Optical detector 450 detects an optical response of syringe 580" to the light generated by light source 430. The optical response of syringe 580" is indicative of the quantity of liquid in syringe 580", and consequently of the dose administered to the patient using syringe 580". A control means 434", in electrical communication with light source 430 and optical detector 450, temporally controls the operation of light source 430 and optical detector 450. Control means 434" turns on light source 430 and optical detector 450 when syringe 580" is appropriately positioned for dose measurements, before and after the administration of the dose to the patient.

A computing means 436" is in electrical communication with optical detector 450 and with a calibration memory 438". Computing means 436" is further in electrical communication with a recording means 440". Computing means 436" generates dose data to be stored in recording means 440". The dose data preferably includes a dose (e.g. an insulin dose) administered to the patient, but may be in general any data which can be used to reconstruct (for example within apparatus 428", at patient computer 424, or at clinician computer 426) the dose administered to the patient. In particular, computing means 436" calculates quantities of liquid within syringe 580" before and after injection of a dose. Computing means 436" then calculates the difference between the two measured liquid quantities, and sends the result (the dose) to recording means 440' for storage.

Computing means 436" determines liquid quantities by comparing optical response data received from optical detector 450 with predetermined calibration data stored in calibration memory 438". The calibration data is indicative of the correspondence between optical responses and liquid quantities for the entire range of potential liquid quantities in syringe 580". That is, calibration memory 438" stores the liquid quantity corresponding to a given optical response of detector 450, for all liquid quantities potentially present in syringe 580".

A monitoring or testing means 444" is electrically connected to recording means 440". Monitoring means 444" tests a physical or physiological condition of the patient, and generates condition data representative of the condition. The condition may be, for example, diabetes; the monitoring means may include a blood glucose meter; and the condition data may include a blood glucose level of the patient. Recording means 440" records the condition data generated by monitoring means 444'. A display 446" is electrically connected to recording means 440", and displays dose data and condition data to the patient. Note that a display such as display 446" may be directly connected to computing means 436" and monitoring means 444", rather than indirectly through recording means 440".

Figure 31B:
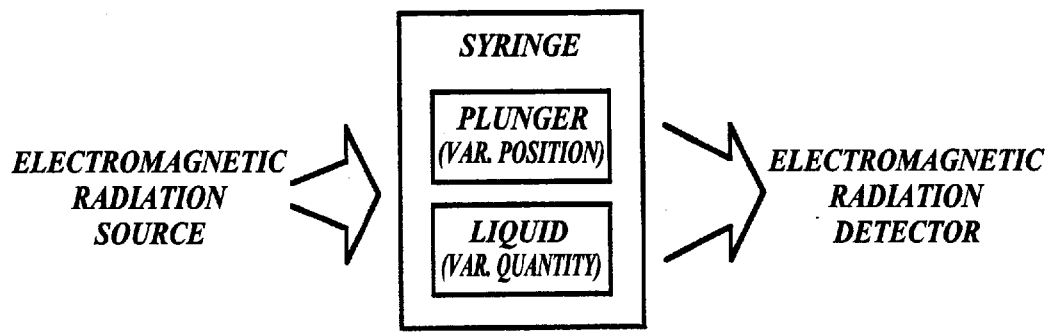
FIG. 31B illustrates broadly the principal detection step performed by the apparatus of FIG. 31A.

FIG. 31B illustrates generally the principal detection step performed by measurement apparatus 428" of the present invention. Light (electromagnetic radiation) is incident on syringe 580" and interacts with syringe 580". Light resulting from the interaction is then incident on detector 450 (FIG. 31A). The light incident on detector 450 may generally be light transmitted, reflected, and/or emitted by syringe 580". In general, two elements of syringe 580" may vary with the quantity of liquid within syringe 580" in a typical dose administration sequence: i) the position of the syringe plunger (relative to the syringe barrel), and ii) the quantity/position of the liquid within syringe 580". Light incident on syringe 580" may interact with the plunger and/or liquid. The measured light interaction with the plunger is preferably substantially different from the interaction with the liquid, such that the interaction with syringe 580" as a whole depends on at least one of the position of the plunger and the quantity of liquid.

Figure 32A:
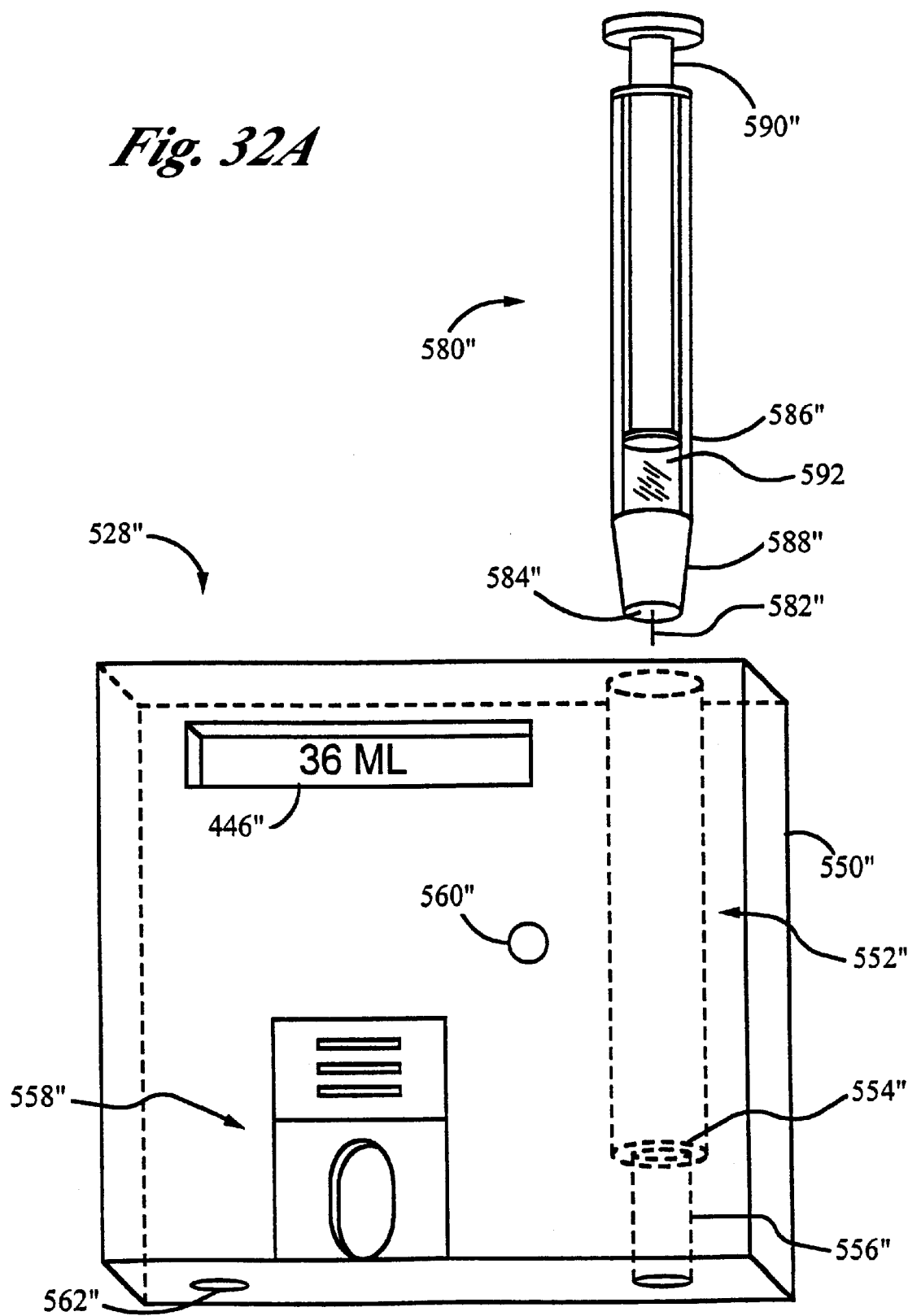
FIG. 32A is a perspective view of a drug delivery measurement apparatus according to another embodiment of the invention.

FIG. 32A shows a perspective view of an apparatus 528", according to a preferred embodiment of the present invention. Apparatus 528" includes a housing 550" enclosing the various electronic and optical components of apparatus 528". Display 446" is recessed within housing 550". A patient interface 558" (of monitoring means 444", FIG. 31A) is also coupled to housing 550". In a preferred embodiment, the patient places his or her finger on patient interface 558", allowing monitoring means 444" to perform a blood glucose measurement for the patient. A dose measurement control 560" of control means 434" is coupled to housing 550", and allows the patient to specify when dose measurements are to be performed by apparatus 528" (see below)

Housing 550" also encloses a holding means 552" for receiving and holding a syringe 580" in a measurement position. Syringe 580" can be a conventional plastic syringe. Syringe 580" includes a barrel 586" and a plunger 590", defining a space for a liquid 592. Plunger 590" is capable of longitudinal motion relative to barrel 586", for adjusting the volume available to liquid 592. Barrel 586" has side walls transparent at a wavelength of light emitted by light source 430 (FIG. 31A), as well as a control portion 588" opaque at a wavelength of light emitted by a control emitter (see below).

Holding means 552" includes an alignment ledge 554" for aligning barrel 586" to holding means 552" in a predetermined measurement position. A contact surface 584" of syringe 580" is in contact with alignment ledge 554" when syringe 580" is in the measurement position (see below). A space 556" accommodates a needle 582" of syringe 580", when the latter is in the measurement position.

FIG. 32B shows a longitudinal sectional view through syringe 580" and holding means 552', with syringe 580" in a measurement position. A light source 1300 and an optical detector 1302 are mechanically coupled to holding means 552", and in optical communication with syringe 580". Optical detector 1302 is opposite light source 1300 relative to syringe 580", such that optical detector 1302 detects light transmitted through syringe 580". Light source 1300 generates light incident on both plunger 590" and liquid 592. A control light source 1304 and a control optical detector 1306 of control means 434" (FIG. 31A) are mechanically coupled to holding means 552", and are in optical communication with control portion 588" (FIG. 32A) when syringe 580" is in the measurement position.

FIG. 32C shows a detail of FIG. 32B. Following a patient command entered by the patient pressing dose measurement control 560" (FIG. 32A), control light source 1304 emits a light beam 1309 which is blocked by control portion 588" when syringe 580" is in the measurement position. If light beam 1309 is blocked, control means 434" operates light source 1300 and detector 1302 to take a first liquid quantity measurement, before the injection of liquid 592 by the patient. Light beam 1309 is then incident on control detector 1306 while syringe 580" is out of holding means 552". When the patient inserts syringe 580" into holding means 552" after the injection of a dose of liquid 592, light beam 1309 is again blocked, and control means 434" operates light source 1300 and detector 1302 to take a second liquid quantity measurement. The difference between the two liquid quantities is taken to be the dose injected by the patient, and is stored by recording means 440".

Light source 1300 includes a plurality of light emitters 1300a–f, while detector 1302 includes a plurality of detecting elements 1302a–f. Light emitters 1300a–f and detecting elements 1302a–f are longitudinally spaced apart at regular intervals. Each light emitter 1300a–f is longitudinally aligned to a corresponding detecting element 1302a–f. Light emitters 1300a–f are preferably narrow-angle light emitting diodes (LEDs), while detecting elements 1302a–f are preferably photodiodes capable of detecting light of a wavelength emitted by light emitters 1300a–f.

For detecting the quantity of liquid 592 within syringe 580", light emitters 1300a–f emit light beams 1308a–f incident on plunger 590" and liquid 592. Detector elements 1302a–f detect the resulting optical response pattern of syringe 580". Emitter 1300d, situated under the current position of plunger 590", emits a light beam 1308d which passes through liquid 592 and is incident on detector 1302d. Emitter 1300e, situated above the current position of plunger 590", emits a light beam 1308e which is incident on plunger 590". Plunger 590" has a substantially different optical transmission property from liquid 592 at the wavelength(s) measured by detecting element 1302e. Preferably, plunger 590" is opaque at those wavelengths. Plunger 590" then substantially blocks beam 1308e, such that beam 1308e is not incident on detecting element 1302e. An electrical signal indicative of the optical pattern detected by detector 1302 is sent to computing means 436".

Figure 32E:
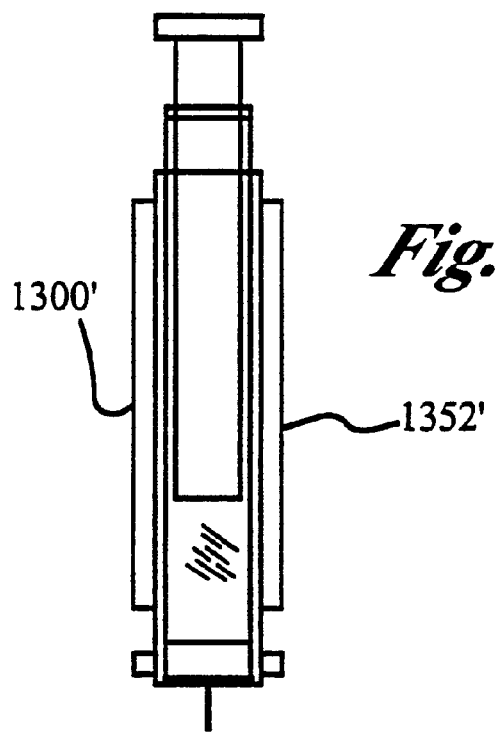
FIG. 32E shows another alternative light source and detector arrangement in a view similar to that of FIG. 32C, according to the invention.

FIG. 32D illustrates an alternative geometry for a detector of the present invention. A detector 1352 includes detecting elements 202a–c, each of which receives light emitted by plural emitters of light source 1300. FIG. 32E illustrates yet another geometry for a light source and detector of the present invention. A light source 1300' and a detector 1352' each comprise a single emitting or detecting element, extending longitudinally over the range of potential plunger bottom positions. The total amount of light detected by detector 1352' is indicative of the plunger position—relatively little light is incident on detector 1352' if the plunger occludes the light path between light source 1300' and detector 1352'. The single-element detecting scheme illustrated in FIG. 32E can be less sensitive than a multiple-element detecting scheme using similar components, but is advantageous because of its simple design.

Figure 33B:
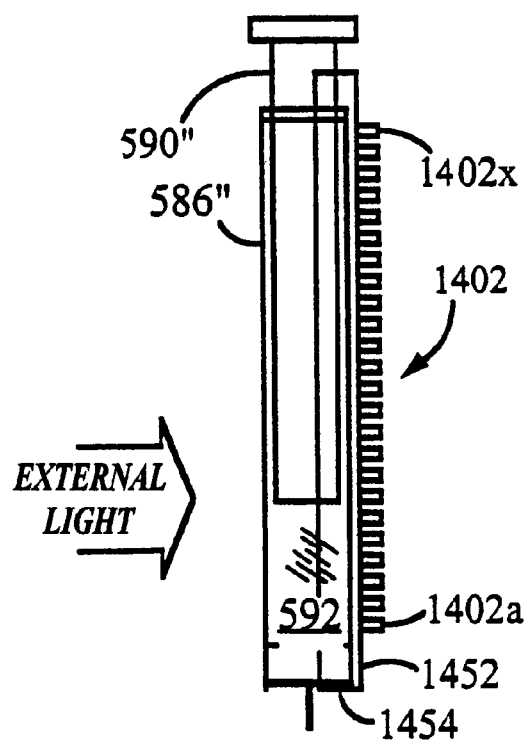
FIG. 33B shows a longitudinal sectional view of a syringe situated in a measurement position in a holder of the apparatus of FIG. 33A.

FIG. 33A shows a perspective view of another embodiment of the present invention. An apparatus 1420 includes a holding means 1452 which encloses syringe 580" only on one side when syringe 580" is in a measurement position. FIG. 33B shows a longitudinal side view of the holding means 1452 and syringe 580" in the measurement position. A control ledge 1454 aligns barrel 586" of syringe 580" with a detector 1402 in the measurement position. Detector 1402 includes plural longitudinally spaced detecting elements 1402a–x. To take measurements, the patient orients the measurement face of holding means 1452 toward an external source of spatially uniform light, preferably a parallel light beam. For example, the patient places apparatus 1452 close to a bright window or lamp. For the embodiment in FIG. 33A, the computing means calculates quantities of liquid within syringe 580" according to the distribution of signals received from the detecting elements of detector 1402, rather than the absolute values of the signals.

FIG. 34 shows a perspective view of another embodiment of the present invention. An apparatus 1528 includes a holding means 1552 for holding the barrel of a syringe 1580 in a predetermined position relative to a measurement window 1503. Syringe 1580 includes a plunger 1590 having a longitudinally varying marking 1591. Marking 1591 is desirably a color marking, but generally may be a shape marking. A light source and detector (both not shown) are situated behind measurement window 1503, for reading the part of marking 1591 in alignment with window 1503. Light emitted by the light source is reflected by marking 1591 back into the detector. The reflected light (its intensity and/or spatial distribution) is indicative of the position of marking 1591 relative to window 1503, which is in turn indicative of the quantity of liquid within syringe 1580. The quantity of liquid within syringe 1580 is in turn indicative of a dose delivered from syringe 1580.

SUMMARY, RAMIFICATIONS, AND SCOPE

Although the above description contains many specificities, these should not be construed as limitations on the scope of the invention but merely as illustrations of some of the presently preferred embodiments. Many other embodiments of the invention are possible. For example, the scripting language and script commands shown are representative of the preferred embodiment. It will be apparent to one skilled in the art that many other scripting languages and specific script commands may be used to implement the invention.

Moreover, the invention is not limited to the specific applications described. The system and method of the invention have many other applications both inside and outside the healthcare industry. For example, pharmaceutical manufacturers may apply the system in the clinical development and post marketing surveillance of new drugs, using the system as an interactive, on-line monitoring tool for collecting data on the efficacy, side effects, and quality of life impact of the drugs. Compared to the current use of labor intensive patient interviews, the system provides a fast, flexible, and cost effective alternative for monitoring the use and effects of the drugs.

The system may also be used by home healthcare companies to enhance the service levels provided to customers, e.g. panic systems, sleep surveillance, specific monitoring of disease conditions, etc. Alternatively, the system may be used to monitor and optimize the inventory of home stationed health supplies. As an example, the system may be connected to an appropriate measuring device to optimize timing of oxygen tank delivery to patients with chronic obstructive pulmonary disease (COPD).

It will be clear to one skilled in the art that the above embodiments may be altered in many ways without departing from the scope of the invention. Generally, the dose data may include, for example, quantities of liquid in the syringe before and/or after the administration of the dose, or dose measurement (capacitive, inductive, or optical) response values before and/or after the administration of the dose. The patient's and/or the clinician's computers then determine the dose administered to the patient from the dose data stored in the recording device. In such an embodiment, calibration data may be stored on the patient's or clinician's computer, and the measurement apparatus may lack a computing device. The patient computer need not be a conventional personal computer, but can be in general any data storage device or device allowing communication between the patient's measurement apparatus and the clinician's data storage device or server. A measurement apparatus of the present invention may connect directly to a clinician's server, rather than indirectly through a patient computer.

Various computation and storage devices used in the present invention may generally be implemented through software or dedicated hardware, or combinations thereof. For a multiple-delivery injection device such as an injection pen, liquid quantities before and after each injection are measured and the administered dose is taken to be the difference between the two quantities. The dose measurement aspects of the present invention are not limited to diabetes care, and may be used for monitoring patient compliance with any injection-based treatment program.

Various capacitor geometries and placements may be suitable in a device of the present invention. In particular, the capacitor need not laterally enclose the syringe completely or even partially, as long as the capacitive element is capacitively coupled to the syringe. The method does not require the presence of a plunger to determine capacitance. A method of the present invention may be used to capacitively measure liquid levels in plungerless syringes operated using air pressure, for example.

Similarly, various inductive element geometries and placements may be suitable in a device of the present invention. In particular, the inductive element need not laterally enclose the syringe completely or even partially, as long as the inductive element is inductively coupled to the syringe. The method does not require the presence of a plunger to determine inductance; a method of the present invention may be used to inductively measure liquid levels in plungerless injection devices operated using air pressure, for example.

With regard to optical based dose measurement embodiments of the invention, detecting spatial distributions is useful for increasing sensitivity. The detector need not detect a spatial distribution of light, however. The detector may detect a spatial sum of light intensity over a whole area, as long as that spatial sum is indicative of the dose administered with the syringe. For example, the detector may detect the total amount of light passing through the syringe, or the total amount of light emitted by the syringe following absorption of incident light (e.g. the total amount of heat emitted following exposure to microwave radiation). Moreover, light emitting and detecting elements need not be longitudinally spaced or aligned, and light beams need not be transverse to the longitudinal axis of the syringe. Various light source and detector geometries and placements may be suitable in a device of the present invention.

An optical method of dose measurement does not require the presence of a plunger to transmit, reflect or absorb light. A method of the present invention may be used to optically measure liquid levels in plungerless syringes operated using air pressure, for example.

The optical dose measurement methods and devices described above may be extended to non-optical wave energy forms such as sound (non-electromagnetic) waves. The considerations discussed above for choosing frequency and detector parameters for optical detectors largely apply to an apparatus using sound wave detection. For example, suitable sound frequencies may include frequencies for which sound absorption by water is significantly (e.g. at least by a factor of two) different from absorption by the syringe plunger. Sound frequencies above the hearing range may be desirable so as to avoid disturbing the user.

Therefore, the scope of the invention should be determined not by the examples given, but by the appended claims and their legal equivalents.

What is claimed is:

1. A system for remotely monitoring a dose of a drug administered to a patient, comprising:
    a) a server;
    b) a remote interface means connected to the server;
    c) a measurement apparatus for providing measurement data related to the patient; and
    d) a remotely programmable apparatus, in communication with said measurement apparatus, for receiving measurement data from said measurement apparatus, said remotely programmable apparatus in communication with said server via a communication network; wherein said measurement apparatus provides drug dose measurement data indicative of the dose.

2. The system of claim 1, wherein said measurement apparatus includes a recording device for recording the drug dose measurement data, said recording device in communication with said remotely programmable apparatus.

3. The system of claim 2, wherein said measurement apparatus further includes: a dose measurement element, and a measuring device in communication with said dose measurement element, said measurement apparatus for measuring a response of said dose measurement element, and wherein said measuring device is in communication with said recording device.

4. The system of claim 3, wherein said dose measurement element comprises a capacitive element or an inductive element.

5. The system of claim 2, wherein said measurement apparatus further includes a monitoring device for monitoring a physiological condition of the patient and for generating a condition datum representative of the physiological condition of the patient, said monitoring device in communication with said recording device such that said recording device records said condition datum.

6. The system of claim 5, wherein said monitoring device comprises a blood glucose meter and said condition datum comprises a blood glucose level of the patient.

7. The system of claim 2, wherein said recording device comprises a digital memory unit.

8. The system of claim 3, wherein said measurement apparatus further includes:
    a display connected to said measuring device, said display for displaying the dose; and
    a computing device in communication with said recording device, said computing device for computing said drug dose measurement data from the response of said dose measurement element.

9. The system of claim 8, wherein said measurement apparatus further includes a calibration memory in communication with said computing device, said calibration memory for providing said computing device with calibration data indicative of a correspondence between the response of said dose measurement element and said drug dose measurement data.

10. The system of claim 4, wherein said measurement apparatus further includes a holder for receiving and holding a syringe in a measurement position.

11. The system of claim 10, further comprising a housing enclosing said measuring device and said recording device, wherein said holder is mechanically coupled to said housing.

12. The system of claim 11, wherein said housing further encloses said holder and said dose measurement element, said housing shielding said dose measurement element and the syringe from external electric fields.

13. The system of claim 10, wherein said holder comprises a well, said well laterally enclosing the syringe in the measurement position, and said dose measurement element is coupled to said well so as to laterally enclose the syringe in the measurement position.

14. The system of claim 10, wherein said dose measurement element comprises a capacitive element, said capacitive element being defined between a liquid held by the syringe and an electrode located external to the syringe, wherein said measurement apparatus further comprises a needle contact coupled to said holder, said needle contact for establishing electrical communication between said measuring device and a needle of the syringe when the syringe is in the measurement position, and said needle is in electrical contact with the liquid.

15. The system of claim 10, wherein said dose measurement element comprises a capacitive element, said capacitive element including:
   a) a first electrically conducting longitudinal plate coupled to said holder; and
   b) a second electrically conducting longitudinal plate coupled to said holder opposite said first longitudinal plate, and said second plate electrically insulated from said first plate.

16. The system of claim 10, wherein said inductive element is coupled to said holder such that an inductive response of said inductive element is indicative of the dose when the syringe is in the measurement position.

17. The system of claim 1, wherein the measurement apparatus further includes:
   a) a syringe having a barrel and an inductance-enhancing element; and
   b) a holder for receiving and holding said syringe in a measurement position, wherein a position of said inductance-enhancing element relative to said barrel of said syringe is indicative of the dose, and wherein said inductive response is indicative of said position of said inductance-enhancing element.

18. The system of claim 17, wherein said syringe includes a plunger, and said inductance-enhancing element comprises a ferromagnetic material, a longitudinal plunger element, a ferromagnetic plunger core, or a plurality of distinct sections arranged longitudinally within said plunger.

19. The system of claim 1, wherein the measurement apparatus further includes:
   a) a holding means for receiving and holding a syringe in a measurement position;
   b) a light source coupled to said holding means and in optical communication with the syringe, for generating light incident on the syringe when said syringe is in the measurement position, wherein an optical response of the syringe to said light is indicative of said dose; and
   c) an optical detector coupled to said holding means and in optical communication with the syringe, for detecting the optical response; wherein said optical detector is in electrical communication with said recording device, said recording device for recording a dose datum indicative of said optical response, wherein said dose datum is indicative of the dose.

20. The system of claim 1, wherein said server includes a script generating means for generating a script program executable by said remotely programmable apparatus to communicate a message to the patient.

21. The system of claim 20, wherein the remotely programmable apparatus comprises:
   i) a communication means for transmitting the measurement data to said server;
   ii) a memory means for storing the script program;
   iii) a user interface means for communicating the message to the patient; and
   iv) a processor means connected to said communication means, said user interface means, and said memory means for executing the script program.

22. The system of claim 20, wherein said remotely programmable apparatus includes:
   i) communication means for receiving the script program from said server and for transmitting to said server responses to the queries;
   ii) user interface means for communicating queries to the patient and for receiving responses to the queries;
   iii) memory means for storing the script program and responses to the queries;
   iv) processor means connected to said communication means, said user interface means, and said memory means for executing the script program to communicate the queries to the patient, to receive the responses to the queries, and to transmit the responses to said server; and
   v) device interface means connected to said processor means for receiving the measurement data from said measurement apparatus; wherein said memory means includes means for storing the measurement data, and said communication means includes means for transmitting the measurement data to said server.

23. A system for remotely monitoring a dose of a drug administered to a patient, comprising:
   a) a server;
   b) a remote interface means connected to the server;
   c) a measurement apparatus for providing measurement data related to the patient; and
   d) a remotely programmable apparatus for receiving measurement data from the measurement apparatus, the remotely programmable apparatus being networked to the server via a communication network; wherein the measurement apparatus includes:
      i) a syringe having a barrel, a plunger, and a response-enhancing element;
      ii) a holding means for receiving and holding said syringe in a measurement position;
      iii) a light source coupled to said holding means and in optical communication with said syringe, for generating light incident on said syringe, wherein an optical response of said syringe to said light is indicative of said dose; and
      iv) an optical detector coupled to said holding means and in optical communication with said syringe, for detecting the optical response;
      v) a recording device in electrical communication with said optical detector; and
      vi) an alignment means for aligning said barrel of said syringe to said optical detector, said recording device for recording a dose datum indicative of said optical response, wherein said dose datum is indicative of the dose.

24. The system of claim 23, wherein a position of a marking of said response-enhancing element is indicative of said dose; and said optical response depends on an interaction of the light with said marking in said position.

25. The system of claim 23, wherein said response-enhancing element comprises a longitudinal element mechanically coupled to said plunger, and said longitudinal element is longitudinally marked.

26. The system of claim 24, wherein said marking comprises a longitudinally-variable color marking which varies longitudinally in brightness or in hue.

27. The system of claim 23, wherein said optical detector is situated opposite said light source relative to said syringe, or adjacent said light: source relative to said syringe.

28. A system for monitoring a patient, comprising:
a) a server;
b) a remote interface means connected to the server;
c) a remotely programmable apparatus for receiving measurement data from the measurement apparatus, the remotely programmable apparatus being networked to the server via a communication network; and
d) an optical dose measurement apparatus, in communication with said server, for providing a dose datum of a drug delivered to the patient from a syringe; wherein the optical dose measurement apparatus includes:
  i) a holding means for receiving and holding the syringe;
  ii) at least one optical detecting element coupled to said holding means and in optical communication with the syringe, for detecting an optical response pattern of the syringe, wherein said optical- response pattern is indicative of the dose; and
  iii) a recording means in electrical communication with said at least one opt i(al detecting element, for recording a dose datum indicative of said optical response pattern, wherein said dose datum is indicative of the dose.

29. A method for remotely monitoring a patient, comprising the steps of:
a) providing the patient with a remotely programmable apparatus and a measurement apparatus in communication with the remotely programmable apparatus, the measurement apparatus having:
  i) a dose measurement, element,
  ii) a measuring device in communication with the dose measurement element for measuring a response of the dose measurement element; and
  iii) a recording device in communication with the measuring device, wherein the measurement apparatus provides measurement data related to the patient;
b) collecting the measurement data in the remotely programmable apparatus;
c) transmitting the measurement data from the remotely programmable apparatus to a server; and
d) receiving and storing the measurement data in the server.

30. The method of claim 29, wherein the remotely programmable apparatus includes:
  i) a communication means for exchanging data between the remotely programmable apparatus and the server through a communication network;
  ii) a memory means for storing the data exchangeable between the remotely programmable apparatus and the server; and
  iii) a processor means connected to the communication means, and the memory means.

31. The method of claim 29, wherein the measurement data related to the patient comprises dose measurement data indicative of a dose of a drug delivered to the patient.

32. The method of claim 29, wherein the dose measurement element comprises a capacitive element or an inductive element.

33. The method of claim 29, wherein the measurement apparatus further includes a recording device and a monitoring device, wherein the monitoring device provides physiological condition measurements to the recording device, the physiological condition measurements indicative of a physiological condition of the patient; wherein the remotely programmable apparatus further includes a device interface connected to the processor means for receiving the physiological condition measurements; and wherein said step b) comprises collecting the physiological condition measurements in the remotely programmable apparatus.

34. The method of claim 33, wherein the physiological condition comprises diabetes, and the physiological condition measurements comprise a blood glucose level of the patient.

35. The method of claim 30, wherein the data exchangeable between the remotely programmable apparatus and the server includes a script program, executable by the remotely programmable apparatus, to communicate queries to the patient, to receive responses to the queries, and to transmit the responses to the server; and wherein the remotely programmable apparatus further includes a user interface mean for communicating the queries to the patient and for receiving the responses to the queries.

36. The method of claim 35, wherein the server comprises a web server having a web page for entry of the queries, and wherein the queries are entered by accessing the web page through the Internet and entering the queries in the web page.

37. A method for communicating information to a patient, the method comprising the steps of:
a) providing the patient with a measurement apparatus and a remotely programmable apparatus in communication with the measurement apparatus, the remotely programmable apparatus having:
  i) a communication means for exchanging data with a server through a communication network, wherein the exchangeable data includes a script program executable by the remotely programmable apparatus to communicate a message to the patient;
  ii) a memory means for storing the script program;
  iii) a user interface for communicating the message; and
  i) a processor means connected to the communication means, the memory means, and the user interface for executing the script program; and the measurement apparatus having:
  vi) a measuring device comprising a dose measurement element, the measuring element for measuring a response of the dose measurement element;
  vii) and a recording device in communication with the measuring device and the remotely programmable apparatus;
b) generating measurement data from the measurement apparatus related to the patient;
c) transmitting the measurement data from the recording device to the remotely programmable apparatus via a standard cable; and
d) transmitting the measurement data from the remotely programmable apparatus to the server through the communication network.

38. The method of claim 37, wherein the measurement apparatus further includes a monitoring device for monitoring a physiological condition of the patient, and wherein the measurement data transmitted in said steps c) and d) includes physiological condition data and dose measurement data.

39. The method of claim 38, wherein the physiological condition data comprises a blood glucose level of a patient, and the dose measurement data comprises a dose of insulin administered to the patient.

40. The method of claim 38, wherein the dose measurement data comprises a dose of a drug administered to the patient from a syringe.

41. The method of claim 40, wherein the syringe includes a plunger, a barrel, and an inductance-enhancing element, wherein a position of the inductance-enhancing element relative to the barrel is indicative of the dose, and the inductance-enhancing element comprises a ferromagnetic material, a longitudinal plunger element, a ferromagnetic plunger core, or a plurality of distinct sections arranged longitudinally within the plunger.

42. The method of claim 40, wherein the measurement apparatus further includes:
   i) a holder for receiving and holding the syringe in a measurement position; and
   ii) a capacitive element coupled to the holder such that a capacitive response of the capacitive element is indicative of the dose when the syringe is in the measurement position; wherein the measuring device is in communication with the capacitive element for measuring the capacitive response; and wherein the recording device is in communication with the measuring device for recording a dose datum indicative of the capacitive response, wherein the dose datum is indicative of the dose.

43. The method of claim 37, wherein the measurement apparatus further includes:
   i) a holder for receiving and holding a syringe in a measurement position,
   ii) a light source in optical communication with the syringe when the syringe is in the measurement position; and
   iii) an optical detector in optical communication with the syringe when the syringe is in the measurement position, the optical detector for detecting an optical response; and the syringe includes a response-enhancing element having a marking, wherein a position of the marking of the response-enhancing element is indicative of the dose.

44. The method of claim 37, further comprising the steps of:
   e) entering in the server the message to be communicated to the patient;
   f) generating the script program in the server;
   g) transmitting the script program from the server to the remotely programmable apparatus through the communication network; and
   h) executing the script program in the apparatus to communicate the message to the patient.

* * * * *